United States Patent
Hao et al.

(10) Patent No.: US 6,924,121 B2
(45) Date of Patent: Aug. 2, 2005

(54) SPERM SPECIFIC PROTEINS

(75) Inventors: Zhonglin Hao, Charlottesville, VA (US); John C. Herr, Charlottesville, VA (US); Friederike L. Jayes, Cary, NC (US); Jagathpala Shetty, Charlottesville, VA (US); Michael J. Wolkowicz, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 126 days.

(21) Appl. No.: 10/181,642

(22) PCT Filed: Jan. 19, 2001

(86) PCT No.: PCT/US01/01717
§ 371 (c)(1),
(2), (4) Date: Jul. 19, 2002

(87) PCT Pub. No.: WO01/53352
PCT Pub. Date: Jul. 26, 2001

(65) Prior Publication Data
US 2003/0087375 A1 May 8, 2003

Related U.S. Application Data

(60) Provisional application No. 60/176,885, filed on Jan. 19, 2000.

(51) Int. Cl.$^7$ .................. A61K 30/395; C07H 21/04; C12N 9/00; C12N 15/09; C12P 21/02
(52) U.S. Cl. .................. 435/69.1; 435/183; 435/320.1; 435/325; 424/146.1; 536/23.1
(58) Field of Search .................. 435/69.1; 530/300, 530/350; 514/2

(56) References Cited

U.S. PATENT DOCUMENTS

| | | |
|---|---|---|
| 5,602,005 A | 2/1997 | Herr et al. |
| 5,830,472 A | 11/1998 | Herr et al. |

FOREIGN PATENT DOCUMENTS

| | | |
|---|---|---|
| WO | WO 98/00486 | 1/1998 |
| WO | WO 99/11293 | 3/1999 |
| WO | WO 00/12708 | 3/2000 |
| WO | WO 01/42451 | 12/2000 |

OTHER PUBLICATIONS

Schellenberger et al. Mapping the S' subsites of serine proteases using acyl transfer to mixtures of peptide nucleophiles. Biochemistry (1993), 32(16), 4349–53.*
Naz, Rajesh K: "Application of Sperm Antigens in Immunocontraception", Frontiers in Bioscience 1, e87–95, Sep. 1 (1996).
O'Hern, Patricia A. et al: "Reversible Contraception in Female Baboons Immunized with a Synthetic Epitope of Sperm–Specific Lactate Dehydrogenase", Biology of Reproduction, vol. 52, pp 331–339, (1995).
DATABASE EMBL 'Online!, Accession No. AF203447, Nov. 12, 2000, Hao, Z. et al.:"Homo Sapiens sperm acrosome membrane protein SAMP32, mRNA, complete cds".
DATABASE EMBL 'Online!, Accession No. AW173256, Nov. 17, 1999, National Cancer Institute, Cancer Genome Anatomy Project (CGAP): "Homo Sapiens cDNA clone".
DATABASE EMBL 'Online!, Accession No. AA824354, Feb. 20, 1998, National Cancer Institute, Cancer Genome Anatomy Project (CGAP): "Homo Sapiens cDNA clone".
DATABASE EMBL 'Online, Accession No. AA31165, May 25, 1997, Hillier, L. et al,: "zw71g10.r1 Soares_testis_NHT Homo sapiens cDNA clone".
DATABASE GENESEQ [Online], Accession No. AAV63171, Jan. 12, 1999, Agostino MJ, et al.: "cDNA from clone cf50_1 which encodes a secreted protein".
DATABASE GENESEQ [ONLINE], Accession No. AAA37094, Aug. 8, 2000, Baker, K et al,: "Human PRO1418 (UNQ732) cDNA Sequence SEQ ID No:264".
DATABASE GENESEQ [ONLINE], Accession No. AAW80397, Jan. 12, 1999, Agostino MJ et al: "A Secreted Protein Encoded by Clone cf50_1".
DATABASE GENESEQ [ONLINE], Accession No. AAY99412, Aug. 8, 2000, Baker, K et al, "Human PRO1418 (UNQ732) Amino Acid Sequence SEQ ID No:265".
Chen, Michellee S., et al.: "Role of the integrin–associated protein CD9 in binding between sperm ADAM 2 and the egg integrin a6b1: Implications for Murine Fertilization", PNAS, vol. 96, No. 21, pp 11830–11835, Oct. 12 (1999).
Le Noir, Francois, et al.: "Severely Reduced Female Fertility in CD9–Deficient Mice", SCIENCE, vol. 287, Jan. 14 (2000).
Diekman, Alan B. et al,: "N–linked glycan of a sperm CD52 glycoform associated with human infertility", FASEB, vol. 13, pp 1303–1308, Aug. (1999).
Miyado, Kenji, et al.: "Reguirement of CD9 on the Egg Plasma Membrane for Fertilization", SCIENCE, vol. 287, Jan. 14 (2000).

* cited by examiner

*Primary Examiner*—Jon Weber
*Assistant Examiner*—Sheridan K Snedden
(74) *Attorney, Agent, or Firm*—Rodney L. Sparks

(57) ABSTRACT

The present invention relates to sperm specific surface proteins, nucleic acid sequences encoding those proteins and antibodies raised against those proteins. Compositions comprising the sperm specific proteins or inhibitors of said proteins can be used in contraceptive applications.

4 Claims, 4 Drawing Sheets

```
              10         20         30         40         50         60
c58        MVLCWLLLLVMALPPGTTGVRDCVFCELTDSMQCPGTYMHCGDDEDCFTGHGVAPGTGPV
              |||  ::|:   |  :  :    |    |    |:|  :|    :  :   ::::   |    |   :   |    |  :
LY6D_HUMAN MRTALLLLAALAVATGPALTLRCHVC--TSSSNCKHSVVCPASSRFCKTTNTVEPLRGNL
              10         20         30           40         50

70         80         90        100        110
c58        INKGCLRATSCGLEEPVSYRGVTYSLTTNCCTGRLCNR----APSSQTVGATTSLALGLG
              ::|   |    |  ||      ::  :    :   :  :|:||     |||:      |    ::|:   |   ::|:|||:
LY6D_HUMAN VKKDC--AESCTPSYTLQGQVSSGTSSTQCCQEDLCNEKLHNAAPTRTALAHSALSLGLA
              60         70         80         90        100        110

120
c58        MLLPPRLL
              : |
LY6D_HUMAN LSLLAVILAPSL
              120
```

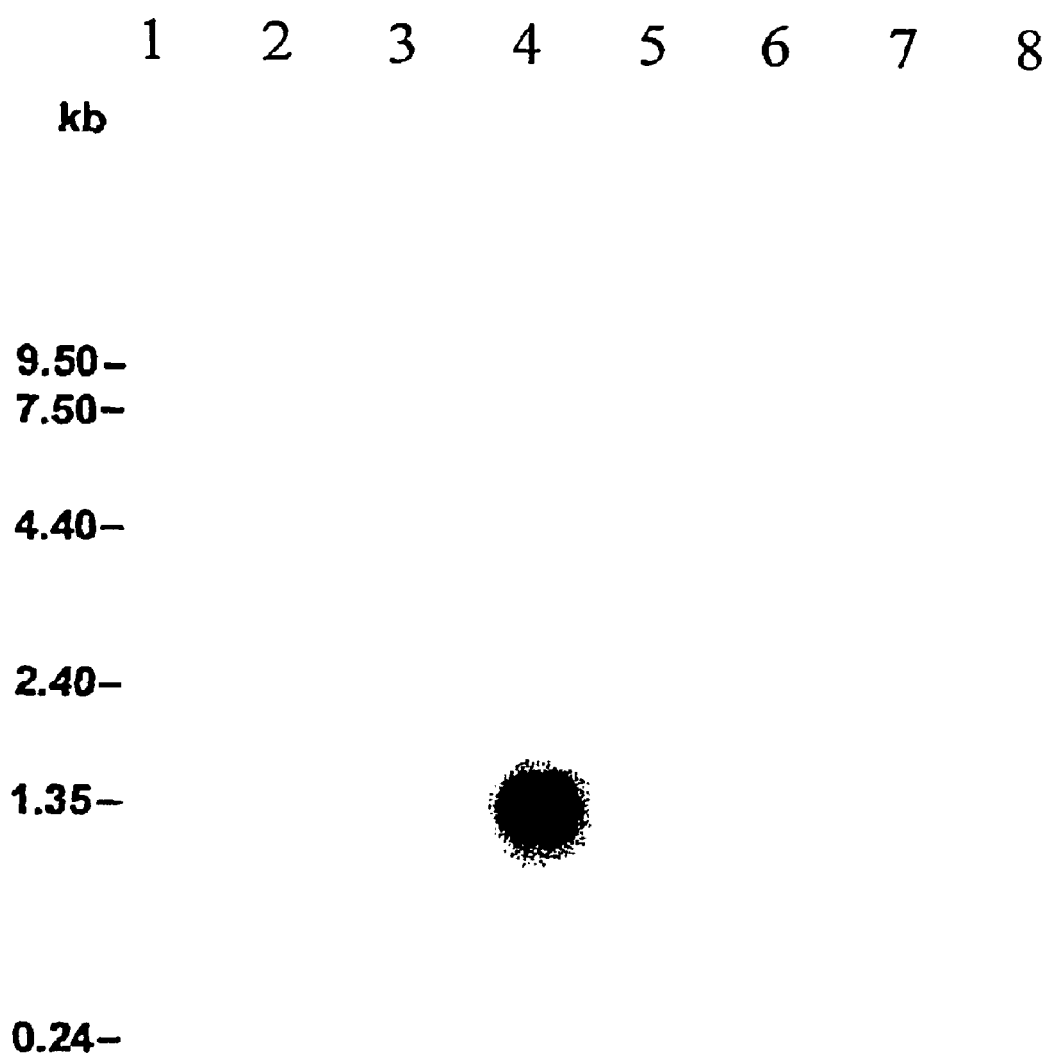

SEQUENCE LISTING

<160> NUMBER OF SEQ ID NOS: 19

<210> SEQ ID NO 1
<211> LENGTH: 1337

-continued

```
<212> TYPE: DNA
<213> ORGANISM: Homo sapiens

<400> SEQUENCE: 1
ccagcctggt ggccccagga cgttccggtc gcatggcaga atgctggggg cgacgcctat      60
gaagccctta gtccttctag ttgcgctttt gctatggcct tcgtctgtgc cggcttatcc     120
gagcataact gtgacacctg atgaagagca aaacttgaat cattatatac aagtttttaga    180
gaacctagta cgaagtgttc cctctgggga gccaggtcgt gagaaaaaat ctaactctcc     240
aaaacatgtt tattctatag catcaaaggg atcaaaattt aaggagctag ttacacatgg     300
agacgcttca actgagaatg atgttttaac caatcctatc agtgaagaaa ctacaacttt     360
ccctacagga ggcttcacac cggaaatagg aagaaaaaa cacacggaaa gtaccccatt      420
ctggtcgatc aaaccaaaca atgtttccat tgttttgcat gcagaggaac cttatattga     480
aaatgaagag ccagagccag agccggagcc agctgcaaaa caaactgagg caccaagaat     540
gttgccagtt gttactgaat catctacaag tccatatgtt acctcataca agtcacctgt     600
caccacttta gataagagca ctggcattga gatctataca gaatcagaag atgttcctca     660
gctctcaggt gaaactgcga tagaaaaacc cgaagagttt ggaaagcacc cagagagttg     720
gaataatgat gacattttga aaaaaatttt agatattaat tcacaagtgc aacaggcact     780
tcttagtgac accagcaacc cagcatatag agaagatatt gaagcctcta agatcacct     840
aaaacccagc cttgctctag cagcagcagc agaacataaa ttaaaaacaa tgtataagtc     900
ccagttattg ccagtaggac gaacaagtaa taaaattgat gacatcgtaa ctgttattaa     960
catgctgtgt aattctagat ctaaactcta tgaatattta gatattaaat gtgttccacc    1020
agagatgaga gaaaaagctg ctacagtatt caatacatta aaaaatatgt gtagatcaag    1080
gagagtcaca gccttattaa agtttattta acaataata taaaaattt aaacctactt      1140
gatattccat aacaaagctg atttaagcaa actgcattt ttcacaggag aaataatcat     1200
attcgtaatt tcaaaagttg tataaaaata ttttctattg tagttcaaat gtgccaacat    1260
ctttatgtgt catgtgttat gaacaatttt catatgcact aaaaacctaa tttaaaataa    1320
aattttggtt caggaaa                                                   1337

<210> SEQ ID NO 2
<211> LENGTH: 350
<212> TYPE: PRT
<213> ORGANISM: Homo sapiens

<400> SEQUENCE: 2

Met Lys Pro Leu Val Leu Leu Val Ala Leu Leu Leu Trp Pro Ser Ser
  1               5                  10                  15

Val Pro Ala Tyr Pro Ser Ile Thr Val Thr Pro Asp Glu Glu Gln Asn
             20                  25                  30

Leu Asn His Tyr Ile Gln Val Leu Glu Asn Leu Val Arg Ser Val Pro
         35                  40                  45

Ser Gly Glu Pro Gly Arg Glu Lys Lys Ser Asn Ser Pro Lys His Val
     50                  55                  60

Tyr Ser Ile Ala Ser Lys Gly Ser Lys Phe Lys Glu Leu Val Thr His
 65                  70                  75                  80

Gly Asp Ala Ser Thr Glu Asn Asp Val Leu Thr Asn Pro Ile Ser Glu
                 85                  90                  95

Glu Thr Thr Thr Phe Pro Thr Gly Gly Phe Thr Pro Glu Ile Gly Lys
            100                 105                 110
```

Lys Lys His Thr Glu Ser Thr Pro Phe Trp Ser Ile Lys Pro Asn Asn
        115                 120                 125

Val Ser Ile Val Leu His Ala Glu Glu Pro Tyr Ile Glu Asn Glu Glu
    130                 135                 140

Pro Glu Pro Glu Pro Glu Pro Ala Ala Lys Gln Thr Glu Ala Pro Arg
145                 150                 155                 160

Met Leu Pro Val Val Thr Glu Ser Ser Thr Ser Pro Tyr Val Thr Ser
                165                 170                 175

Tyr Lys Ser Pro Val Thr Thr Leu Asp Lys Ser Thr Gly Ile Glu Ile
            180                 185                 190

Tyr Thr Glu Ser Glu Asp Val Pro Gln Leu Ser Gly Glu Thr Ala Ile
        195                 200                 205

Glu Lys Pro Glu Glu Phe Gly Lys His Pro Glu Ser Trp Asn Asn Asp
    210                 215                 220

Asp Ile Leu Lys Lys Ile Leu Asp Ile Asn Ser Gln Val Gln Gln Ala
225                 230                 235                 240

Leu Leu Ser Asp Thr Ser Asn Pro Ala Tyr Arg Glu Asp Ile Glu Ala
                245                 250                 255

Ser Lys Asp His Leu Lys Pro Ser Leu Ala Leu Ala Ala Ala Ala Glu
            260                 265                 270

His Lys Leu Lys Thr Met Tyr Lys Ser Gln Leu Leu Pro Val Gly Arg
        275                 280                 285

Thr Ser Asn Lys Ile Asp Asp Ile Val Thr Val Ile Asn Met Leu Cys
    290                 295                 300

Asn Ser Arg Ser Lys Leu Tyr Glu Tyr Leu Asp Ile Lys Cys Val Pro
305                 310                 315                 320

Pro Glu Met Arg Glu Lys Ala Ala Thr Val Phe Asn Thr Leu Lys Asn
                325                 330                 335

Met Cys Arg Ser Arg Arg Val Thr Ala Leu Leu Lys Val Tyr
            340                 345                 350

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: primer_bind
<222> LOCATION: (1)..(22)

<400> SEQUENCE: 3
cttgctctag cagcagcaga ac                                              22

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(30)

<400> SEQUENCE: 4
tcataacaca tgacacataa agatgttggc                                      30

<210> SEQ ID NO 5
<211> LENGTH: 43

<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(43)

<400> SEQUENCE: 5
catgcatgcc atggatccga gcataactgt gacacctgat gaa         43

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(44)

<400> SEQUENCE: 6
gagtcgctcg agataaactt ttaataaggc tgtgactctc cttg        44

<210> SEQ ID NO 7
<211> LENGTH: 14
<212> TYPE: PRT
<213> ORGANISM: Homo sapiens

<400> SEQUENCE: 7

Ala Ser Thr Pro Glu Val Gln Ser Glu Gln Ser Ser Val Arg
 1               5                  10

<210> SEQ ID NO 8
<211> LENGTH: 1455
<212> TYPE: DNA
<213> ORGANISM: Homo sapiens

<400> SEQUENCE: 8
gcgcttcgac gtacctgtcc tcaggagccg cggcggcgac tgcgcctcgg acggccgtcg      60
gggccgagaa ccatgagccc caggggcacg ggctgctccg ccgggctgct gatgactgtc     120
ggctggctgc ttctggcggg cctccagtcc gcgcgcggga ccaacgtcac cgctgccgtc     180
caggatgccg gcctggccca cgaaggcgag ggcgaggagg agaccgaaaa caacgacagc     240
gagaccgcgg agaactacgc tccgcctgaa accgaggatg tttcaaatag gaatgtcgtc     300
aaagaagtag aattcggaat gtgcaccgtt acatgtggta ttgggggttag agaagttata     360 ttaacaaatg gatgccctgg tggtgaatcc aagtgtgttg tacgggtaga gaatgccgt     420 ggaccaacag attgtggctg gggtaaacca atttcagaaa gtcttgaaag tgttagattg     480
gcatgtattc acacatctcc cttaaatcgt ttcaaatata tgtggaaact tctaagacaa     540
gaccaacaat ccattatact tgtaaatgat tcagcaatcc tagaagtacg caaggaaagt     600
caccccttgg ctttcgagtg tgacacactg ataataatg aaatagtagc aactattaaa     660
ttcacagtct atacgagcag tgaattgcag atgagaagat caagcctacc agccactgat     720
gcagccctaa ttttttgtgct gaccatagga gtcattatct gtgtatttat aattttctta     780
ttgatcttca taatcataaa ttgggcagca gtcaaggctt ttggggggc aaaagcctct     840 acacctgagg tacaatccga gcagagttct gtgagataca agattcaac ttctcttgac     900 caattaccaa cagaaatgcc tggtgaagat gatgctttaa gtaatggaa tgaatgatgt     960 ttgaatgata tataacaaac caaaggatat tacagaatat tagattcatt attacaaaaa    1020

-continued

```
taaaatacac attgaaatac tttaataatg ttgcgatgga ttgccacagt gtgaaggaaa    1080
tgcagtgtgg ggataggact attttatcag tgcatttttc cagtacagtt atcaaatatt    1140
acttttaatt tgttctcaac acttatttca ggtaatagct tggggatatt tatctaaagt    1200 accccccaaca aatcttctaa gtgcatttt  gatcactttg ataacttctt aggtgatttg    1260
cctgttttgt cttaaataag aacaatgtaa tatagaaatg ctttacatat tagactttct    1320
ctcccctgga agcactgggt tgaacttgct aaagtaaatc atactttaga atctcttcag    1380
ggaatgtgac atacaaagtt tgtaagacat gaagtaataa cgataatgat aacaataaat    1440
gcttacttag tgaaa                                                    1455
```

<210> SEQ ID NO 9
<211> LENGTH: 294
<212> TYPE: PRT
<213> ORGANISM: Homo sapiens

<400> SEQUENCE: 9

```
Met Ser Pro Arg Gly Thr Gly Cys Ser Ala Gly Leu Leu Met Thr Val
 1               5                  10                  15

Gly Trp Leu Leu Leu Ala Gly Leu Gln Ser Ala Arg Gly Thr Asn Val
                20                  25                  30

Thr Ala Val Gln Asp Ala Gly Leu Ala His Glu Gly Glu Gly Glu
         35                  40                  45

Glu Glu Thr Glu Asn Asn Asp Ser Glu Thr Ala Glu Asn Tyr Ala Pro
     50                  55                  60

Pro Glu Thr Glu Asp Val Ser Asn Arg Asn Val Val Lys Glu Val Glu
 65                  70                  75                  80

Phe Gly Met Cys Thr Val Thr Cys Gly Ile Gly Val Arg Glu Val Ile
                 85                  90                  95

Leu Thr Asn Gly Cys Pro Gly Gly Glu Ser Lys Cys Val Val Arg Val
            100                 105                 110

Glu Glu Cys Arg Gly Pro Thr Asp Cys Gly Trp Gly Lys Pro Ile Ser
        115                 120                 125

Glu Ser Leu Glu Ser Val Arg Leu Ala Cys Ile His Thr Ser Pro Leu
    130                 135                 140

Asn Arg Phe Lys Tyr Met Trp Lys Leu Leu Arg Gln Asp Gln Gln Ser
145                 150                 155                 160

Ile Ile Leu Val Asn Asp Ser Ala Ile Leu Glu Val Arg Lys Glu Ser
                165                 170                 175

His Pro Leu Ala Phe Glu Cys Asp Thr Leu Asp Asn Asn Glu Ile Val
            180                 185                 190

Ala Thr Ile Lys Phe Thr Val Tyr Thr Ser Ser Glu Leu Gln Met Arg
        195                 200                 205

Arg Ser Ser Leu Pro Ala Thr Asp Ala Ala Leu Ile Phe Val Leu Thr
    210                 215                 220

Ile Gly Val Ile Ile Cys Val Phe Ile Ile Phe Leu Leu Ile Phe Ile
225                 230                 235                 240

Ile Ile Asn Trp Ala Ala Val Lys Ala Phe Trp Gly Ala Lys Ala Ser
                245                 250                 255

Thr Pro Glu Val Gln Ser Glu Gln Ser Val Arg Tyr Lys Asp Ser
            260                 265                 270

Thr Ser Leu Asp Gln Leu Pro Thr Glu Met Pro Gly Glu Asp Asp Ala
        275                 280                 285
```

Leu Ser Glu Trp Asn Glu
    290

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(22)

<400> SEQUENCE: 10
agtcacccct tggctttcga gt                                           22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(24)

<400> SEQUENCE: 11
aatattctgt aatatccttt ggtt                                         24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(24)

<400> SEQUENCE: 12
ctttgtatgt cacattccct gaag                                         24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: PCR Primer
<220> FEATURE:
<221> NAME/KEY: primer_bind
<222> LOCATION: (1)..(24)

<400> SEQUENCE: 13
gaggtacaat ccgagcagag ttct                                         24

<210> SEQ ID NO 14
<211> LENGTH: 600
<212> TYPE: DNA
<213> ORGANISM: Homo sapiens

<400> SEQUENCE: 14
gtcccggatc cgcgagggac gcaggcgtt gggaacagag gacactccag gcgctgaccc    60
tgggaggcca ggaccagggc caaagtcccg tgggcaagag gagtcctcag aggtccttca   120
ttcagcggtt ccgggaggtc tgggaagccc acgcctggc tggggcaggg tcaacgccgc   180
caggccgcca tggtcctgtg ctggctgctg cttctggtga tggctctgcc cccaggcacg   240

```
acgggcgtca aggactgcgt cttctgtgag ctcaccgact ccatgcagtg tcctggtacc      300
tacatgcact gtggcgatga cgaggactgc ttcacaggcc acgggtcgc cccgggcact      360 ggtccggtca tcaacaaagg ctgcctgcga gccaccagct gcggccttga ggaacccgtc      420
agctacaggg gcgtcaccta cagcctcacc accaactgct gcaccggccg cctgtgtaac      480
agagccccga gcagccagac agtggggcc accaccagcc tggcactggg gctgggtatg      540
ctgcttcctc acgtttgct gtgaccaaca gggaggacag ggcctgggac tgttcttcca      600
```

<210> SEQ ID NO 15
<211> LENGTH: 375
<212> TYPE: DNA
<213> ORGANISM: Homo sapiens

<400> SEQUENCE: 15

```
atggtcctgt gctggctgct gcttctggtg atggctctgc ccccaggcac gacgggcgtc       60
aaggactgcg tcttctgtga gctcaccgac tccatgcagt gtcctggtac ctacatgcac      120
tgtggcgatg acgaggactg cttcacaggc cacggggtcg ccccgggcac tggtccggtc      180
atcaacaaag gctgcctgcg agccaccagc tgcggccttg aggaacccgt cagctacagg      240 ggcgtcaccct acagcctcac caccaactgc tgcaccggcc gcctgtgtaa cagagccccg      300
agcagccaga cagtggggc caccaccagc ctggcactgg ggctgggtat gctgcttcct      360
ccacgtttgc tgtga                                                       375
```

<210> SEQ ID NO 16
<211> LENGTH: 124
<212> TYPE: PRT
<213> ORGANISM: Homo sapiens

<400> SEQUENCE: 16

```
Met Val Leu Cys Trp Leu Leu Leu Val Met Ala Leu Pro Pro Gly
  1               5                  10                  15

Thr Thr Gly Val Lys Asp Cys Val Phe Cys Glu Leu Thr Asp Ser Met
                 20                  25                  30

Gln Cys Pro Gly Thr Tyr Met His Cys Gly Asp Asp Glu Asp Cys Phe
             35                  40                  45

Thr Gly His Gly Val Ala Pro Gly Thr Gly Pro Val Ile Asn Lys Gly
         50                  55                  60

Cys Leu Arg Ala Thr Ser Cys Gly Leu Glu Glu Pro Val Ser Tyr Arg
 65                  70                  75                  80

Gly Val Thr Tyr Ser Leu Thr Thr Asn Cys Cys Thr Gly Arg Leu Cys
                 85                  90                  95

Asn Arg Ala Pro Ser Ser Gln Thr Val Gly Ala Thr Thr Ser Leu Ala
            100                 105                 110

Leu Gly Leu Gly Met Leu Leu Pro Pro Arg Leu Leu
        115                 120
```

<210> SEQ ID NO 17
<211> LENGTH: 569
<212> TYPE: DNA
<213> ORGANISM: Homo sapiens

<400> SEQUENCE: 17

```
gcactggtcc ggtcatcaac aaaggctgcc tgcgagccac cagctgcggc cttgaggaac       60
ccgtcagcta caggggcgtc acctacagcc tcaccaccaa ctgctgcacc ggccgcctgt      120
gtaacagagc cccgagcagc cagacagtgg gggccaccac cagcctggca ctggggctgg      180
```

-continued

```
gtatgctgct tcctccacgt ttgctgtgac caacagggag gacagggcct gggactgttc    240
tcccagatcc gccactcccc atgtccccat gtccttcccc cactaaatgg ccagagaggc    300
cctggacaac ctcttgcggc cctggcttca tcccttctaa ggctgtccac caggagcccg    360
gtgctagggg aagcatcccc aggcctgact gagcggcagg ggagcacggc ccgtgggttt    420
gattgtatta ctctgttcca ctggttctaa gacgcagagc ttctcacatc tcaatcagga    480
tgcttctctc cattggtagc actttagagt ccatgaaata tggtaaaaaa tatatatata    540
tcataataaa tgacagctga tgttcaaaa                                      569

<210> SEQ ID NO 18
<211> LENGTH: 166
<212> TYPE: DNA
<213> ORGANISM: Homo sapiens

<400> SEQUENCE: 18
atggtcctgt gctggctgct gcttctggtg atggctctgc ccccaggcac gacgggcgtc     60
aaggactgcg tcttctgtga gctcaccgac tccatgcagt gtcctggtac ctacatgcac    120
tgtggcgatg acgaggactg cttcacaggc cacggggtcg ccccgg                   166

<210> SEQ ID NO 19
<211> LENGTH: 13
<212> TYPE: PRT
<213> ORGANISM: Homo sapiens

<400> SEQUENCE: 19

Ala Thr Ser Cys Gly Leu Glu Glu Pro Val Ser Tyr Arg
 1               5                  10
```

SPERM SPECIFIC PROTEINS

This application claims priority under 35 U.S.C. §119(e) to provisional patent application No. 60/176,885, filed Jan. 19, 2000.

US GOVERNMENT RIGHTS

This invention was made with United States Government support under Grant No. HD U54 29099, awarded by the National Institutes of Health. The United States Government has certain rights in the invention.

FIELD OF THE INVENTION

The present invention is directed to sperm specific proteins that have been isolated using 2-D gel analysis and microsequencing of the isolated proteins. These proteins are excellent candidates for use in contraceptive compositions, including contraceptive vaccine compositions.

BACKGROUND OF THE INVENTION

Substantially continuous attention is focused on the development of improved contraceptive methods. One widely exploited technology is the use of spermicides, essentially a chemical barrier that prevents penetration of sperm to the uterus or egg, or inhibits the activity thereof, thereby precluding fertilization One of the most widely used spermicides is a detergent, Nonoxynol-9. Reports indicate an increased incidence of urogenital infections and cervico-vaginal inflammation in women employing this detergent spermicide. McGroarty et al, Journal of Urology, 152(3) :831–833 (1994).

As an alternative to chemical detergents, authors have suggested the use of monoclonal antibodies as likely safe active agents for topical applications, such as use in topical spermicides. See, e.g., Cone et al, Am. J. Reprod. Immunol., 32:114–131 (1994). Studies conclude that in addition to the reduction or elimination of unwanted immune reactions, human monoclonal antibodies should present safe spermicides since their dose and duration of application can be readily controlled, topical delivery minimizes systemic exposure and the monoclonal antibody can be selected for safety and efficacy. Therefore, a sperm-active monoclonal antibody delivered as a topical spermicide may produce desired anti-fertility effects without the negative side effects accompanied by detergent spermicides. See generally, Alexander, Scientific American, September:136–141 (1995). Accordingly, a goal in the art continues to be the provision of a safe and effective spermicide employing monoclonal antibodies.

Many investigators around the world are looking at the possibility of the development of contraceptive vaccines based on sperm antigens. See, e.g., Aitken et al, British Medical Journal, 49:88–99 (1993), Preemerman et al, Biol. Reprod., 50:615–621 (1994) and Herr, Fertility Control, pp. 431–452 (Second Edition 1994). In this connection, work continues on human chorionic gonadotropin (hCG) as a contraceptive vaccine for women. Talwar, Current Opinion in Immunology, 6:698–704 (1994) and European Patent 86304274.3. While clinical vaccine trials are underway with this potential vaccine, the hCG immunogen employed functions as an abortifactant, that is, immune responses induced by inoculation with this vaccine induce abortion of the early embryo or fetus. This may constitute an unacceptable form of contraceptive for many individuals.

As an alternative, a variety of sperm surface antigens have been employed in studies involving primate and rodent models. Thus, decreased fertility rates resulted from the immunization of test animals with sperm surface antigens such as LDH-C4, O'Hern et al, Biol. Reprod., 52:331–339 (1995), PH-20, Primakoff et al, Nature, 335:543,546 (1988), RSA-1, O'Rand et al, J. Reprod. Immunol., 25:89–102 (1993) and fertilin, Ramarao et al, Mol. Reprod. Dev., 43:70–75 (1995). Disappointingly, in primates, the highest rate of efficacy observed with a sperm antigen is about 75 percent inhibition of fertility, O'Hern et al, supra. Thus to date there has not been identified a human sperm antigen that functions as a contraceptive vaccine with a level of efficacy comparable to that of oral contraception. Thus, it remains an object of those of skill in the art to provide a safe and effective contraceptive vaccine with a high rate of fertility inhibition, on the order of the level of efficacy given by oral contraceptives.

Additionally, because those receiving a contraceptive vaccine will require periodic monitoring of serum antibody to determine if they are "safe", use of the sperm specific antigen as a target in assays to measure antibody concentration in persons receiving the vaccine is desirable.

"Over the counter" assay or diagnostic kits for the detection of hormones associated with pregnancy (hCG and others) have achieved wide-spread success in the marketplace, as an alternative or a first-step to potentially embarrassing, inconvenient and expensive visits to medical offices. In recent years, attention has been focused on assays for the presence, and concentration of sperm in a users ejaculate. Both from the point of view of fertility counseling, as well as clinical diagnosis in the case of rape, or for the purposes of assaying for the presence and effectiveness of a vasectomy, a convenient test kit, that could be safely and reliably employed at home, for the detection of sperm in a sample, has become increasingly desirable. In accordance with the present invention, a test kit employing a monoclonal antibody against any of the sperm antigens disclosed herein, is also within the scope of the present invention.

Purification of the sperm specific antigens is the first step in preparation of an effective vaccine. The purified antigen, incorporated in a pharmaceutically acceptable carrier, can be administered to patients desiring vaccination for contraception. Repeated vaccination results in the generation of antibodies against sperm, highly effective in the binding of sperm. To monitor the development of an effective level of antibodies, the purified antigen may be used as a test standard reagent, to determine the presence and amount of antibodies present in the patient, through conventional diagnostics.

Definitions

In describing and claiming the invention, the following terminology will be used in accordance with the definitions set forth below.

As used herein, "nucleic acid," "DNA," and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "peptide" encompasses a sequence of 3 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —$CH_2$-carbamate linkage (—CH$_2$OC(O)NR—), a phosphonate linkage, a —CH$_2$ sulfonamide (—CH$_2$ S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl;

2. peptides wherein the N-terminus is derivatized to a —NRR$_1$ group, to a —NRC(O)R group, to a —NRC(O)OR group, to a —NRS(O)$_2$R group, to a —NHC(O)NHR group where R and R$_1$ are hydrogen or C$_1$-C$_4$ alkyl with the proviso that R and R$_1$ are not both hydrogen;

3. peptides wherein the C terminus is derivatized to —C(O)R$_2$ where R$_2$ is selected from the group consisting of C$_1$-C$_4$ alkoxy, and —NR$_3$R$_4$ where R$_3$ and R$_4$ are independently selected from the group consisting of hydrogen and C$_1$-C$_4$ alkyl.

Naturally occurring amino acid residues in peptides are abbreviated as recommended by the IUPAC-IUB Biochemical Nomenclature Commission as follows: Phenylalanine is Phe or F; Leucine is Leu or L; Isoleucine is Ile or I; Methionine is Met or M; Norleucine is Nle; Valine is Vat or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid. Other naturally occurring amino acids include, by way of example, 4-hydroxyproline, 5-hydroxylysine, and the like.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for trytophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" are defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys;
IV. Large, aliphatic, nonpolar residues:
   Met Leu, Ile, Val, Cys
V. Large, aromatic residues:
   Phe, Tyr, Trp As used herein, the term "purified" and like terms relate to the isolation of a molecule or compound in a form that is substantially free of contaminants normally associated with the molecule or compound in a native or natural environment.

As used herein, the term "C7/8 polypeptide" and like terms refers to polypeptides comprising SEQ ID NO: 2 and biologically active fragments thereof.

As used herein, the term "SAMP32 polypeptide" and like terms refers to polypeptides comprising SEQ ID NO: 9 and biologically active fragments thereof.

As used herein, the term "C58 polypeptide" and like terms refers to polypeptides comprising SEQ ID NO: 16 and biologically active fragments thereof.

As used herein, the term "biologically active fragments" or "bioactive fragment" of an C7/8, SAMP32 or C58 polypeptide encompasses natural or synthetic portions of those polypeptides that are capable of specific binding to at least one of the natural ligands of the native polypeptide.

"Operably linked" refers to a juxtaposition wherein the components are configured so as to perform their usual function. Thus, control sequences or promoters operably linked to a coding sequence are capable of effecting the expression of the coding sequence.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

SUMMARY OF THE INVENTION

The present invention is directed to the isolation and characterization of novel testis and sperm-specific proteins that are expressed on the surface of sperm. In particular the present invention describes three sperm specific protein, C7/8, SAMP23, and C58. These proteins, and fragments thereof, are used in contraceptive vaccine formulations. The application is also directed to antibodies directed against these proteins.

BRIEF DESCRIPTION OF THE DRAWINGS

FIG. 3 is an alignment of the C58 and Ly6D (E48 Antigen) Human amino acid sequences. The two amino acid sequences share 28.8% identity in 118 aa overlap region.

FIG. 4 is a copy of a multiple tissue Northern Blot, wherein C58 cDNA was radiolabeled with p$^{32}$ and hybridized to 2 ug poly-(A)+ mRNAs, revealing a message only in testicular RNA. Size of molecular weight markers is indicated at left, lanes 1–8 contain poly-(A)+ mRNA isolated from spleen, thymus, prostate, testis, ovary, small intestinem colon and leucocyte, respectively.

DETAILED DESCRIPTION OF THE INVENTION

Figure 1:
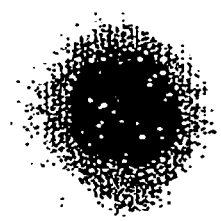
FIG. 1 is a copy of a multiple tissue Northern Blot, wherein C7/8 cDNA was radiolabeled with P$^{32}$ and hybridized to 2 ug poly-(A)+ mRNAs, revealing a message only in testicular RNA. Size of molecular weight markers is indicated at left, lanes 1–8 contain poly-(A)+ mRNA isolated from spleen, thymus, prostate, testis, ovary, small intestinem colon and leucocyte, respectively.

The present invention is directed to therapeutic and diagnostic methods and compositions based on sperm specific surface proteins and the nucleic acids encoding those proteins. In particular the present invention describes the isolation and characterization of three novel proteins, C7/8, SAMP23 and C58 that are expressed in human sperm cells. Antagonists of C7/8, SAMP23 and C58 polypeptide function can be used to interfere with the binding and fusion of the sperm and the egg, and thus such agents can be used as contraceptive agents. Furthermore, antibodies against the C7/8, SAMP23 and C58 polypeptides can be used for the diagnosis of conditions or diseases characterized by expression or overexpression of C7/8, SAMP23 or C58 polypeptides, or in assays to monitor patients being treated with C7/8, SAMP23 or C58 agonists, antagonists or inhibitors.

In one embodiment, the present invention is directed to a purified polypeptide comprising an amino acid sequence selected from the group consisting of SEQ ID NO: 2, SEQ ID NO: 9, SEQ ID NO: 16 and amino acid sequences that differs from SEQ ID NO: 2, SEQ ID NO: 9 or SEQ ID NO: 16 by one or more conservative amino acid substitutions. More preferably, the purified polypeptide comprises an amino acid sequence that differs from SEQ ID NO: 2, SEQ ID NO: 9 or SEQ ID NO: 16 by 20 or less conservative amino acid substitutions, and more preferably by 10 or less conservative amino acid substitutions. Alternatively, the polypeptide may comprise an amino acid sequence that differs from SEQ ID NO: 2, SEQ ID NO: 9 or SEQ ID NO: 16 by 1 to 5 alterations, wherein the alterations are independently selected from a single amino acid deletion, insertion or substitution.

In one embodiment, the present invention provides methods of screening for agents, small molecules, or proteins that interact with C7/8, SAMP23 or C58. The invention encompasses both in vivo and in vitro assays to screen small molecules, compounds, recombinant proteins, peptides, nucleic acids, antibodies etc. which bind to or modulate the activity of C7/8, SAMP23 or C58 and are thus useful as therapeutics or diagnostic markers for fertility.

In one embodiment the C7/8 polypeptide, or bioactive fragments thereof, is used to isolate ligands that bind to the C7/8 polypeptide under physiological conditions. The method comprises the steps of contacting the C7/8 polypeptide with a mixture of compounds under physiological conditions, removing unbound and non-specifically bound material, and isolating the compounds that remain bound to the C7/8 polypeptides.

In another embodiment the SAMP23 polypeptide, or bioactive fragments thereof, is used to isolate ligands that bind to the SAMP23 polypeptide under physiological conditions. The method comprises the steps of contacting the SAMP23 polypeptide with a mixture of compounds under physiological conditions, removing unbound and non-specifically bound material, and isolating the compounds that remain bound to the SAMP23 polypeptides.

In one embodiment the C58 polypeptide, or bioactive fragments thereof, is used to isolate ligands that bind to the C58 polypeptide under physiological conditions. The method comprises the steps of contacting the C58 polypeptide with a mixture of compounds under physiological conditions, removing unbound and non-specifically bound material, and isolating the compounds that remain bound to the C58 polypeptides.

Typically, the C7/8, SAMP23 or C58 polypeptide will be bound to a solid support using standard techniques to allow rapid screening compounds. The solid support can be selected from any surface that has been used to immobilize biological compounds and includes but is not limited to polystyrene, agarose, silica or nitrocellulose. In one embodiment the solid surface comprises functionalized silica or agarose beads. Screening for such compounds can be accomplished using libraries of pharmaceutical agents and standard techniques known to the skilled practitioner.

In accordance with one embodiment an antigenic composition is provided wherein the composition comprises a polypeptide selected from the group consisting of SEQ ID NO: 2, SEQ ID NO: 9, SEQ ID NO: 16 and antigenic fragments of the polypeptides of SEQ ID NO: 2, SEQ ID NO: 9 or SEQ ID NO: 16. The compositions can be combined with a pharmaceutically acceptable carrier and administered to a patient to induce an immune response. In one embodiment of the invention, antibodies directed to the C7/8, SAMP23 or C58 polypeptides, and fragments thereof, can be administered to provide passive immunity and thereby provide a contraceptive effect.

The present invention encompasses vaccines useful for contraception. In one aspect of the invention C7/8, SAMP23 or C58 polypeptides, or antigenic fragments thereof, are delivered to a subject to elicit an active immune response. The vaccine acts as a temporary and reversible antagonist of the function of the sperm surface proteins of the invention. For example, such vaccines could be used for active immunization of a subject, to raise an antibody response to temporarily block sperm's ability to bind or fuse to the egg.

In another aspect of the invention C7/8, SAMP23 or C58 polypeptides, or antigenic fragments thereof, are used as vaccines for permanent sterilization of a subject. Such vaccines can be used to elicit a T-cell mediated attack on the individuals sperm cells as a method for irreversible sterilization. Methods for generating T-cell specific responses, such as adoptive immunotherapy, are well known in the art (see, for example, Vaccine Design, Michael F. Powell and Mark J. Newman Eds., Plenum Press, New York, 1995, pp 847–867). Such techniques may be particular useful for veterinary contraceptive or sterilization purposes, where a single dose vaccination may be desirable.

The preparation of vaccines containing an immunogenic polypeptide as the active ingredient is known to one skilled in the art (see, for example, Vaccine Design, Michael F. Powell and Mark J. Newman Eds., Plenum Press, New York, 1995, pp 821–902). The vaccines of the invention may be multivalent or univalent. Methods of introducing the vaccine may include oral, intravaginal, intradermal, intramuscular, intraperitoneal, intravenous, subcutaneous, intranasal, and via scarification (scratching through the top layers of skin, e.g., using a bifurcated needle) or any other standard routes of immunization. The immunopotency of the C7/8, SAMP23 and C58 polypeptide antigens can be determined by monitoring the immune response in test animals following immunization with the those protein antigens, or by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

Suitable preparations of vaccines include injectables, either as liquid solutions or suspensions, however, solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

Examples of adjuvants which may be effective, include, but are not limited to: aluminum hydroxide, N-acetylmuramyl-L-threonyl-D-isoglutamine (thr-MDP), N-acetylnor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine. The effectiveness of an adjuvant may be determined by measuring the induction of antibodies directed against an immunogenic polypeptide containing a C7/8, SAMP23 or C58 polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of one or more of the sperm surface proteins of the present invention, and more particularly a polypeptide, or antigenic fragment thereof, selected from the group consisting of C7/8, SAMP23 and C58 polypeptides, and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration. The composition, if desired, can also contain minor amounts of wetting or emulsifying agents, or pH buffering agents.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered. Effective doses (immunizing amounts) of the vaccines of the invention may also be extrapolated from dose-response curves derived from animal model test systems.

In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

The present invention thus provides a method of immunizing an animal, comprising administering to the animal an effective immunizing dose of a vaccine of the present invention.

Another embodiment of the present invention comprises antibodies that are generated against an antigen selected from the C7/8, SAMP23 or C58 polypeptides. These antibodies can be formulated with standard carriers and optionally labeled to prepare therapeutic or diagnostic compositions. The antibodies generated against C7/8, SAMP23 or C58 antigens have potential uses in vaccination against fertilization, sterilization, diagnostic immunoassays, passive immunotherapy, and generation of antiidiotypic antibodies.

Antibodies to the C7/8, SAMP23 and C58 polypeptides may be generated using methods that are well known in the art. Such antibodies may include, but are not limited to, polyclonal, monoclonal, chimeric (i.e "humanized" antibodies), single chain (recombinant), Fab fragments, and fragments produced by a Fab expression library. These antibodies can be used as diagnostic agents for the diagnosis of conditions or diseases characterized by expression or overexpression of the C7/8, SAMP23 or C58, or in assays to monitor patients being treated with C7/8, SAMP23 or C58 receptor agonists, antagonists or inhibitors. The antibodies useful for diagnostic purposes may be prepared in the same manner as those described above for therapeutics. The antibodies may be used with or without modification, and may be labeled by joining them, either covalently or non-covalently, with a reporter molecule.

In one embodiment the antibodies generated against C7/8, SAMP23 or C58 polypeptides are used in passive immunotherapy, in which short-term protection of a host is achieved by the administration of pre-formed antibody directed against a heterologous organism. The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, 1974, Ann. Immunol. (Paris) 125c:373; Jerne, et al., 1982, EMBO J. 1:234).

In accordance with one embodiment an antibody is provided that specifically binds to a protein selected from the group consisting of SEQ ID NO: 2, SEQ ID NO: 9 and SEQ ID NO: 16. In one preferred embodiment the antibody is a monoclonal antibody. Compositions can be prepared in accordance with the present invention comprising one or more antibodies directed against epitopes present on C7/8, SAMP23 or C58 and a pharmaceutically acceptable carrier. In one embodiment the antibody is a monoclonal antibody.

The invention also encompasses antibodies, including anti-idiotypic antibodies, antagonists and agonists, as well as compounds or nucleotide constructs that inhibit expression of the C7/8, SAMP23 or C58 gene (transcription factor inhibitors, antisense and ribozyme molecules, or gene or regulatory sequence replacement constructs). The present invention also encompasses compositions that can be placed in contact with sperm cells to inhibit the function of the C7/8, SAMP23 or C58 protein (i.e. either by inhibiting the expression of the C7/8, SAMP23 or C58 protein or by interfering with the protein's function). In particular the compositions may comprise peptide fragments of the respective C7/8, SAMP23 or C58 polypeptides, or analogs thereof that are taken up by the sperm cells and compete for binding with the native polypeptide's natural ligands. Such inhibitory peptides can be modified to include fatty acid side chains to assist the peptides in penetrating the sperm cell membrane. Compositions comprising an agent that inhibits C7/8, SAMP23 or C58 functionality can be used to modulate fertility of an individual, and in one embodiment, the inhibitory agents function as a male contraceptive pharmaceutical. In accordance with one embodiment a composition is provided that comprises an eight to fifteen amino acid sequence that is identical to an eight to fifteen consecutive amino acid sequence of SEQ ID NO: 2, SEQ ID NO: 9 or SEQ ID NO: 16 and a pharmaceutically acceptable carrier.

The present invention also encompasses nucleic acid sequences that encode the C7/8, SAMP23 or C58 polypeptide, as well as bioactive fragments and derivatives thereof. In particular, the present invention is directed to nucleic acid sequences comprising a sequence selected from the group consisting of SEQ ID NO: 1, SEQ ID NO: 8, SEQ ID NO: 14 and SEQ ID NO: 15, or fragments thereof. In one embodiment, a purified nucleic acid comprising at least 25 contiguous nucleotides that are identical to any 25 contiguous nucleotides of SEQ ID NO: 1 are provided. In another embodiment, a purified nucleic acid comprising at least 25 contiguous nucleotides that are identical to any 25 contiguous nucleotides of SEQ ID NO: 8 are provided. In another embodiment, a purified nucleic acid comprising at least 25 contiguous nucleotides that are identical to any 25 contiguous nucleotides of SEQ ID NO: 14 are provided. In other embodiments, the nucleic acid sequence comprises at least 50 (contiguous) nucleotides, 100 nucleotides, 200 nucleotides, or 500 nucleotides of a sequence selected from the group consisting of SEQ ID NO: 1, SEQ ID NO: 8, SEQ ID NO: 14 and SEQ ID NO: 15.

The present invention also includes nucleic acids that hybridize (under conditions defined herein) to all or a portion of the nucleotide sequence represented by SEQ ID NO:1, SEQ ID NO: 8 or SEQ ID NO: 14 or their complement sequences. The hybridizing portion of the hybridizing nucleic acid is typically at least 15 (e.g., 20, 25, 30, or 50) nucleotides in length. Hybridizing nucleic acids of the type described herein can be used, for example, as a cloning probe, a primer (e.g., a PCR primer), or a diagnostic probe. It is anticipated that a DNA sequence selected from the group consisting of SEQ ID NO: 1, SEQ ID NO: 8 or SEQ ID NO: 14, or fragments thereof can be used as probes to detect additional members of the C7/8, SAMP23 or C586 families, respectively, and to detect homologous genes from other vertebrate species.

Nucleic acid duplex or hybrid stability is expressed as the melting temperature or Tm, which is the temperature at which a nucleic acid duplex dissociates into its component single stranded DNAs. This melting temperature is used to define the required stringency conditions. Typically a 1% mismatch results in a 1° C. decrease in the Tm, and the temperature of the final wash in the hybridization reaction is reduced accordingly (for example, if two sequences having >95% identity, the final wash temperature is decreased from the Tm by 5° C.). In practice, the change in Tm can be between 0.5° C. and 1.5° C. per 1% mismatch.

The present invention is directed to the nucleic acid sequences of SEQ ID NO: 1, SEQ ID NO: 8, SEQ ID NO: 14 and SEQ ID NO: 15 and nucleic acid sequences that hybridize to that sequence (or fragments thereof) under stringent or highly stringent conditions. In accordance with the present invention highly stringent conditions are defined as conducting the hybridization and wash conditions at no lower than −5° C. Tm. Stringent conditions are defined as involve hybridizing at 68° C. in 5×SSC/5× Denhardt's solution/1.0% SDS, and washing in 0.2×SSC/0.1% SDS at 68° C. Moderately stringent conditions include hybridizing at 68° C. in 5×SSC/5× Denhardt's solution/1.0% SDS and washing in 3×SSC/0.1% SDS at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In another embodiment of the present invention, nucleic acid sequences encoding the C7/8, SAMP23 or C58 polypeptide can be inserted into expression vectors and used to transfect cells to expression of those respective proteins in the target cells. In accordance with one embodiment, nucleic acid sequences encoding C7/8, SAMP23 or C58, or a fragment or a derivative thereof, are inserted into a eukaryotic expression vector in a manner that operably links the gene sequences to the appropriate regulatory sequences, and the polypeptide is expressed in a eukaryotic host cell. Suitable eukaryotic host cells and vectors are known to those skilled in the art. In particular, nucleic acid sequences encoding a C7/8, SAMP23 or C58 polypeptide may be added to a cell or cells in vitro or in vivo using delivery mechanisms such as liposomes, viral based vectors, or microinjection. Accordingly, one aspect of the present invention is directed to transgenic cell lines that contain recombinant genes that express a polypeptide selected from the group consisting of C7/8, SAMP23 or C58.

In accordance with one embodiment the recombinant C7/8, SAMP23 or C58 polypeptides are be produced in large amounts and purified for use in vaccine preparations. Alternatively, the recombinant C7/8, SAMP23 or C58 polypeptides of the invention also have utility in immunoassays, e.g., to detect or measure in a sample of body fluid from a vaccinated subject the presence of antibodies to the antigen, and thus to diagnose and/or to monitor immune response of the subject subsequent to vaccination.

Osteoglycin-like Sperm Glycoprotein C7/8

Detection of Con-A binding proteins was carried out by exposing a Western blot of 2-D electrophoretically separated total sperm proteins to peroxidase-conjugated Con-A. Subsequently, the Con-A was visualized by DAB counterstaining and demonstrated a number of positive regions at 30, 40, 45, 75 and 90 kDa. More importantly, a region from 32 to 36 kDa and 5.0 to 5.0 pI that reacted positively was evident. The positive staining with Con-A indicated then that this region of the 2-D contained a protein that was glycosylated and therefore was of possible secretory or surface origin.

Western blots of electrophoretically 2-D separated sperm proteins probed with pools of fertile and infertile serum from 5 male and 5 female individuals each were also examined. After incubation with peroxidase-conjugated anti-human IgG and counterstaining with DAB a repetoire of different proteins from the male and female infertile individuals versus control seras from fertile males and females was revealed. A number of areas were highly immunogenic in the both the male fertile and infertile sera such as a broad pI-region around 90 kDa, a series of proteins between 60 to 90 kDa of pI 5.5 to 6.0 as well as others. Likewise, infertile female sera recognized some of these same areas to varying degrees as well as others. Interestingly, a region around 34–38 kDa and 5.1 pI was found to be weakly immunogenic in male sera, indicating autoantigenicity, but was not recognized by either of the two fertile seras. Due to the remarkable correlation with the previous Con-A results for this region it was decided to examine the proteins in this region further.

Two protein spots having relative molecular weights of 33 and 35 kDa and estimated pIs of 5.0 and 5.1 respectively, were excised from a Coomassie stained 2-D gel. Microsequencing of peptides derived from tryptic digestion of the protein spots were performed by both Edman degradation and tandem mass spectrometry yielding a set of peptide sequences. A number of peptides from each protein spot were found to shared by both protein spots (Peptides 4, 6 and 7 of C7 corresponding to peptides 7, 9 and 10 of C8, respectively). Analysis of these protein fragments by comparison to the non-redundant and EST NCBI databases revealed a few ESTs with significant matches to all three peptides found in common to both proteins (Assession numbers: AA913806, AI33709, AI123225, AA432186, AI027115, AA782995, AA431165). Moreover, the 3 peptides were found to be contained in the same open reading frame (ORF) in these ESTs lending support to the hypothesis that these peptides were all part of some common protein. Further database analysis with these ESTs did not reveal any significant match to any known proteins and therefore this protein was deemed to be new and unique and therefore of interest to our laboratory.

Oligonucleotides were manufactured to ends of the EST and a PCR reaction was performed with reverse transcribed human testicular cDNA. A PCR product of the proper electrophoretic mobility was collected and sequenced before $^{32}$P-labeling and used as a probe of a human testicular λDR2 cDNA library. After purification of several positive phage isolates the largest clone was sequenced in both directions. The nucleic acid sequence (SEQ ID NO: 1) of the cDNA library clone was 1337 bp in length and contained two start codons, both at the beginning of the same contiguous ORF at bp 41 and at bp 59. Utilizing the methionine at bp 59 as the start codon the ORF predicts a protein of 350 amino acids in length (SEQ ID NO: 2) and 37.0 kDa in molecular weight with cleavage of the signal peptide and 39.6 kDa without this post-translational modification. Both of these predictions agree well with the region of the 2-D gel from which this protein spot was originally cored. A pI of either 5.4 or 5.44 was also predicted for the cleaved and uncleaved proteins respectively, likewise agreeing well with the original positioning on the 2-D gel system.

Further examination of the predicted protein revealed a consensus N-glycosylation site, NVSI, (Miletich and Broze, 1990) starting at amino acid 134. The presence of a glycosylation site lends credence to the assumption that the proper protein spot was cloned. Numerous cAMP (starting at amino acid 119 and 347; Glass et al., 1983), PKC (starting at amino acids 66, 129, 182, 296, 339 and 346; Woodget et al., 1986) and casein kinase2 (starting at amino acids 32, 85, 91, 188, 194, 200 and 212; Pinna, 1990) consensus phosphorylation sites were also found. Finally, the original three peptide sequences used to identify the EST were present starting at amino acid positions 264–274, 310–317 and 328–335. Another peptide microsequence was discovered at amino acids 179–186 that was not included in the original EST translated ORF further reinforcing the conclusion that the proper cDNA clone was assigned to the 2-D protein spot.

The complete ORF was subjected to analysis by database searching. Utilization of Blast identified a 29% identical and 49% homologous to match to a portion of murine osteoglycin (Ujita et al., 1995). Osteoglycin is a glycoprotein (Bentz et al., 1990) originally isolated from bovine osteoblasts (Madisen et al., 1990), human osteocarcinoma sources and vascular smooth muscle cells (Shanahan et al., 1997). Osteoglycin belongs to a larger family of leucine-rich-repeat proteins that include a number of extracellular matrix proteoglycans (Kajava, 1998; Matsuuhima et al., 2000). The 68 amino acid region encompassing residues 67–134 of murine osteoglycin (Ujita et al., 1995) aligns with amino acids 272–337 of the C-terminal region of C7/8. Notable in this region is a conserved serine residue that is implicated in covalent linking of osteoglycin with extracellular matrix components. Likewise, the ProDomo algorithim (Altshul et al., 1990) identified a 50% homology to the CDC24 family of guanine nucleotide releasing factors over the 154–206 amino acid range of C7/8 and a 50% homology from amino acids 274–304 to type II membrane binding proteins.

To ascertain the tissue specificity of the gene transcript a Northern blot containing mRNA from various human tissues was probed with the radiolabeled C7/8 cDNA (FIG. 1). A single prominent band of approximately 1.5 Kb was observed only in the lane containing testicular mRNA. The size of the mRNA transcript in the autoradiogram also verified that, in all probability, a near full-length cDNA had been isolated. Probing the blot with radiolabeled β-actin (not shown) was performed as a quality control for the mRNA on the membrane. As opposed to these results with a sperm-specific osteoglycin-like cDNA bovine osteoglycin cDNA applied to Northern blots reveals 2 transcripts of 1.9 and 2.4 Kb in size and is restricted to cells of the bone lineage (Madisen et al., 1990). An array of 76 different human tissue mRNAs were then hybridized to a radiolabeled C7/8 on a dot-blot to examine a larger repetoire of tissues. The results confirmed that the C7/8 is indeed transcribed in adult testis.

In order localize and characterize human C7/8 (h-C7/8) a monospecific polyclonal sera was generated for immunological studies. The h-C7/8 ORF was expressed in *E. coli* using a pET28 plasmid (Novagen). Oligonucleotides bracketing the ORF were designed and the cloning was carried out as described in Example 1. Induction of the plasmid-bearing *E. coli* with 1 mM IPTG in a 20 ml shake-flask was performed at an approximate $OD_{600}$ of 0.7 and 1.0 OD-ml samples were removed at 1 hr intervals for 3 hrs. The culture expressing h-C7/8 doubled in $OD_{600}$ during the 3 hr time period as opposed to a 30 min doubling time before induction.

Purified rec-h-C7/8 was utilized to generate a monospecific polyclonal antisera in virgin female Lewis rats. Western blotting 1-D gels was employed to test the antisera generated against the recombinant protein. The primary and secondary antibodies alone (lanes 1 and 2, respectively) failed to recognize rec-h-tekB1 whereas primary and secondary antibodies together reacted with the recombinant immunogen. When an extract of human sperm proteins was separated on 2-D gels, transferred to a nitrocellulose membrane and sequentially Gold- and immuno-stained with rat-rec-h-tekB1 three h-tekB1 isoforms were specifically immunostained. These three h-tekB1 isoforms migrated at a identical molecular weight (53.5 kDa) but varied slightly in charge with pI's from 5.25 to 5.35. This observation indicates that there are three differently modified forms of the h-tekB1 present in human sperm.

The rat α-rec-h-C7/8 sera was utilized to examine the immunohistochemical localization of the C7/8 protein within human sperm. Live staining of human sperm was negative indicating that the C7/8 protein was not located in an accessible region of the human sperm. However, when mounted and permeabilized human sperm were probed with the rat α-rec-h-C7/8 sera, counter-stained and examined a different result was obtained. Preimmune sera used as a control demonstrated no fluorescence while the immune sera reacted positively with a banded region of the human sperm localized to the base of the acrosome. This pattern of staining was consistent in all the sperm observed although occasional sperm demonstrated a punctate granular localization. In all likelihood the localization of the human C7/8 protein is in the equitorial segment of the human sperm.

To definitively prove the localization of the human C7/8 protein human sperm were subjected to electronmicroscopic examination. Staining was performed with the rat α-rec-h-C7/8 sera, and data showed that the immunogold beads are predominantly present within the equitorial segment of the human sperm. The equitoral segment of the human sperm is a specialized region of the acrosome known previously to be involved with membrane fusion events of the sperm with the egg as opposed to purely binding events. Accordingly it is anticipated that the C7/8 protein may participate in sperm binding and fusion with the egg. Therefore compounds that interfere with C7/8 function will provide effective contraceptive agents.

Sperm Acrosomal Membrane Protein 32 (SAMP32)

Sperm Acrosomal Membrane Protein 32 (SAMP32) was initially isolated from 2-D gels and was initially designated "C71". In particular, human sperm proteins, partitioned into the Triton X-114 detergent phase, were resolved by isoelectric focusing (IEF) in the first dimension, and by SDS-PAGE in the second dimension. Protein spots from the Commassie-stained gels were then cored for sequencing by mass spectrometry. Among the several dozens of sperm proteins sequenced were four spots named C71, 72, 74, and 75. These spots shared the same peptide sequence according to the mass-spectrometry analysis (ASTPEVQSEQSSVR, SEQ ID NO: 7, was the longest). Interestingly however, their apparent molecular weights varied from 30 to 34 kD and their pIs ranged from 4.5 to 5.5. Vectorial labeling showed that at least one of the four spots (C74) could be labeled by using biotin.

When the peptide sequence of SEQ ID NO: 7 was used in database search, no known genes were found in the non-redundant protein database suggesting that it is a novel protein. There were, however, two exact matches from the expressed sequence tag database (Entry AI419884 and AI809484) which overlap each other. Two oligo DNA primers, based on AI419884, were then designed to amplify cDNA from the human testis cDNA library by PCR, which was followed by confirming DNA sequencing. By screening the lambda DR2 human testis cDNA library with the cDNA fragment as probe, 16 clones were picked up in the secondary round. Of these, clone 1-4-1 (1050 bp) had the largest size. Subsequent DNA sequencing confirmed that AI419884 was embedded in it. A 3'RACE was done to amplify the full length clone (1455) as the expressed sequence tag (EST) database search and northern blot suggested a short of 400 bp in 3'UTR of clone 1-4-1. The full-length clone is 1455 bp nucleotide long (SEQ ID NO: 8) and contains a contiguous open reading frame of 294 amino acids (SEQ ID NO: 9). The predicted molecular weight and pI are 32 kD and 4.57 respectively. A FASTA search against the current database, using the full-length open reading frame, revealed homology to two genes from different species. They are malaria Circumsporozoite protein CSP and fission yeast KRP1.

Circumsporozoite protein is the immunodominant surface antigen on the sporozoite. The sporozoite is the infective stage of the malaria parasite that is transmitted from the mosquito to the vertebrate host. CSP consists of 358 amino acids, the first 19 amino acids contain a signal peptide and amino acids 98–277 contain repeat that are thought to be important in anchoring the protein to membranes. There repeat units are not found in SAMP32. The amino terminus of SAMP32 shares 30.088% identity and 53.09% similarity in a 113 amino acid region (amino acids 22–131 of SAMP32 compared to 259–366 of CSP).

Dibasic Processing Endoprotease Precursor (KRP1) is required for cell vaibility in fission yeast. It is a subtilisin-like serine protease that cleaves P-factor precursor and other precursors. This protein belongs to the type I membrane proteins and to peptidase family S8. The carboxy terminus of SAMP32 shares 25.309% identity and 51.85% similarity in a 162 amino acid region (amino acids 123–263 of SAMP32 compared to 551–707 of KRP1).

SAMP32 is Phosphorylated in vivo and is a Predicted Transmembrane

By running the algorithms provided in the PredictProtein program, three possible sites for phosphorylation by Casein Kinase II were disclosed. Of these, at lease one, i.e. the serine residue at amino acid position 256, was shown to be phosphorylated in vivo by mass spectrometry analysis of peptide sequences. In addition, the protein architecture was analyzed with algorithms provided in the Simple Modular Architecture Research Tool on the ExPASy server. This analysis revealed a signal peptide from amino acid 1 to 29, a low complexity region from amino acid 39 to 61 and a transmembrane domain from amino-acid 222 to 242. The low complexity region is comprised mainly of glutamic acid (35% ). In addition, prediction indicated possible N-Glycosylation of three amino acid residue(s) at aa31, 54, and 155.

Expression of SAMP32 is Exclusively Testis

Figure 2:
FIG. 2 is a copy of a multiple tissue Northern Blot, wherein SAMP32 cDNA was radiolabeled with p$^{32}$ and hybridized to 2 ug poly-(A)+ mRNAs, revealing a message only in testicular RNA. Size of molecular weight markers is indicated at left, lanes 1–8 contain poly-(A)+ mRNA isolated from spleen, thymus, prostate, testis, ovary, small intestinem colon and leucocyte, respectively. The lower panel of FIG. 2 shows the identical blot probed with @-actin cDNA as a positive control.

To examine the expression of SAMP32 in various tissues, a multi-tissue northern blot was done first. A DNA fragment containing the entire ORF of SAMP32 was used as a probe. As shown in FIG. 2, SAMP32 was only detected in testis in a total of 8 tissues including spleen, thymus, prostate, ovary, small intestine, colon and peripheral lymphocytes, which suggested that SAMP32 is testis specific. This specificity was further confirmed by RNA dot blot hybridization. In this experiment, $^{32}$P labeled SAMP32 was used to probe a membrane dotted with RNA samples extracted from 67 human tissues. In agreement with the multi-tissue northern blot result, only testis yield a hybridization signal.

When the entire cDNA sequence of SAMP32 was searched against the human genomic database, SAMP32 was localized to 6q15–16.2 of chromosome 6 (Genebank entry, AL136096). Comparison of the cDNA sequence with the corresponding genomic sequence revealed that SAMP32 consists of a total of 7 exons ranging from 60 bp to 650 bp long. They were distributed across a 19 kb region on chromosome 6. In all cases, the nearly invariant splicing consensus GU and AG in the 5 prime and 3 prime end of the intron have been found.

To study the SAMP32 gene expression at the protein level, antiserum against recombinant SMARC32 was generated Part of the open reading frame of SAMP32 was amplified by PCR, inserted into pET28b expression vector and expressed in *E. coli*. Purified protein as a single band on SDS-PAGE was used to inject the rats. Antiserum produced was used to blot human total sperm protein extracted with TritonX114. The antiserum detected mainly three bands with apparent molecular weights of 54, 48, and 41 Kd respectively and the 48 Kd band was the most abundant one quantitatively. The size of the molecular weight and the result of the western blot using the recombinant protein indicated that the high molecular weight bands are likely dimers. To determine if this antiserum recognizes protein spots that were cored from the two-dimensional gel, proteins that were extracted with TritonX-114 and partitioned into TritonX-114, were loaded onto a two dimensional gel. After transfer to nitrocellulose membrane, protein spots were detected using the same antiserum as described above.

Considering the hypothesis that SAMP32 is a putative transmembrane phosphoprotein, the antibody agains SAMP32 was used to localized its position on human spermatozoa. The antiserum stained the whole acrosomal cap and the equatorial bar of human spermatozoa in immunofluorescence staining. The same antiserum stained mainly the inner and the outer acrosomal membrane alone with some staining of matrix, which strongly suggested that SAMP32 is acrosome-associated protein located in the sperm acrosome, hence the name Sperm Acrosome Membrane-associated Protein (SAMP32).

To follow SAMP32 expression in-situ during acrosomal development, human testis were from clinical patients. The tissue was digested with trypsin, micrococcal nuclease and collagenase. The dissociated cell smear on slides were then stained with rat anti-rSMARC antiserum. The sperm nuclei were counter-stained with DAPI at the same time to facilitate localization. SAMP32 was present in all stages of acrosome development including the Golgi phase, the cap phase in the round spermatids, the acrosomes of elongating spermatids as well as the elongated mature sperm. The patterns are just like those found in SP10, a known acrosomal associated molecule.

To determine the fate of SAMP32 after the acrosomal reaction fresh sperm were washed and acrosomal reactions were induced by incubation progesterone. The acrosomal reacted sperm were stained first using SAMP32 as primary antibody and TRITC-conjugated donkey anti-rat Ig as secondary antibody. This was followed by staining with Con-A conjugated with FITC. By staining SAMP32 in acrosomal reacted sperm it was shown that SAMP32 is still associated with equatorial segment following capacitation and acrosomal reaction. Thus it is anticipated that SAMP32 plays an important role in sperm egg interaction and thus in an appropriate immunological target for contraceptive vaccines.

Sperm Membrane Protein C58

Differential solubilization and phase partitioning using TX-114 followed by 2-D gel electrophoresis was used to identify a novel, hydrophobic, putative human sperm membrane protein, which was named C58. The cDNA of the protein was cloned using a human testis EST. Notable features of C58 are: 1) a 19 aa amino terminal signal peptide, 2) a Ly-6/urokinase plasminogen activator receptor like domain (aa 22–112), 3) a potential transmembrane domain near the carboxy terminus, (aa 101–124), and 4) a carboxy terminal cleavage site for transamidase, (aa 97–99) suggesting C58 is glycosylphosphatidylinositol (GPI) anchored. Transcripts for C58 were expressed only in testis as studied by Northern blot of 8 human tissues and by dot blot analysis of 76 human tissue RNAs.

Recombinant C58 was produced in *E. coli* using the pET 28b vector. Antibody against the recombinant protein was successfully generated in rats. The antibody reacted with a sperm protein at an expected molecular weight of 12.5 kDa on 1-D gels and recognized the native 2-D spot that was initially cored for microsequencing C58. Preliminary experiments on the indirect immunofluorescence localization of the protein revealed that it is on the entire surface of the human sperm. The bioinformatic study of the c-DNA derived amino acid sequence revealed that it is a putative GPI anchored protein belonging to the Ly-6 family.

The location of C58 on the entire surface of the human sperm and the fact that the protein is expressed only in sperm make this protein an ideal target for contraceptive agents. In accordance with one embodiment an antigenic composition is provided comprising an antigen selected from the group consisting of SEQ ID NO: 16 or antigenic fragments thereof. In addition, compositions comprising a nucleic acid comprising the nucleic acid sequence of SEQ ID NO: 18 are also provided.

EXAMPLE 1

Isolation and Characterization of C7/8 2-D Electrophoresis, Standard Protein Gels and Western Blotting Human sperm proteins for 2-D gel electrophoresis were solubilized and separated as previously described by Naaby-Hansen et al. (1997). Briefly, fresh semen specimens were allowed to liquify for up to 3 h before centrifugation on two-layer (80% and 55% in Ham s F-10 medium) Percoll density gradients. After subsequent washing of the sperm pellet collected from the bottom of the 80% gradient 3 times in Ham s F-10 medium, the sperm were solubilized in a lysis buffer consisting of 2% (v:v) NP-40, 9.8 M urea, 100 mM DTT, 2% ampholines (pH 3.5–10) and a cocktail of protease inhibitors before performing isoelectric focusing on 0.15 mg of sperm proteins in a 15×0.15 cm acrylamide rod containing a carrier ampholine (Pharmacia) composition of 28% pH 3.5–5, 20% pH 5–7, 7% pH 7–9 and 45% pH 3.5–10 in a gel composition described previously (Naaby-Hansen et al., 1997). Prior to electrophoresis the tubes containing the sperm protein extract were overlayed with a buffer containing 5% NP-40, 1% ampholines (pH 3.5–10), 8 M urea and 100 mM DTT. Isoelectric focusing was conducted in steps: 2 h at 200 V, 5 h at 500 V, 4 h at 800 V, 6 h at 1200 V and 3 h at 2000 V. Second dimensional electrophoresis was performed by laying the isoelectrically focused tube gel onto a 0.15×20 cm linear (9–15% acrylamide) slab gel in a Protean II xi Multi-Cell apparatus (Bio-Rad).

Standard SDS-PAGE gel electrophoresis (Coligan et al., 1995) for recombinant proteins and prokaryotic cell lysates were performed on 16×18 cm gel electrophoresis apparatus (BioRad) with 0.75 mm spacers with 12% polyacrylamide separating gels. Protein or cellular samples were either suspended in standard Laemmli Buffer and boiled for 10 min before addition to the gel or treated with iodoacetic acid by the procedure of Crestfield et al. (1963). Standard *E. coli* lysates consisted of 1 OD-ml of bacterial culture, pelleted before suspension in loading buffer.

Electrophoretic transfer to nitrocellulose membranes of separated proteins was performed in Transblot Buffer (25 mM Tris (pH 8.3), 192 mM Glycine and 20% Methanol) for 1 A-Hr. The membranes were either utilized intact for 2-D gels or cut into strips for standard protein gels, blocked with 5% fat-free dry milk in PBS-Tween (1×PBS (pH 7.4), 0.05% Tween) and incubated with either rat antisera or pools of fertile or infertile sera from 5 individuals in blocking buffer for 1 hr. Immunodetection was performed with horseradish peroxidase-conjugated goat anti-rat IgG (Jackson ImmunoResearch) at a 1:5000 dilution in blocking buffer and visualized with diaminobenzidine (Sigma) in $H_2O_2$ or TMB (KPL).

Screening of the 2-D blot with Con-A was performed by incubating Western transferred 2-D gels of human sperm proteins first with TBS (10 mM Tris-HCl (pH 8.0), 150 mM NaCl) then with TBS containing 1% gelatin (TBSG) for 1 hr (Auer et al., 1995). After rinsing in TBS, the membrane was incubated with peroxidase-conjugated Con-A (5 μg/ml) in TBSG containing 1 mM $MCl_2$ and 1 mM $CaCl_2$ cations for 1 hr at room temperature before rinsing briefly twice with TBSG. After washing the membrane 4 times for 15 min each with TBSG/cations staining was performed with diaminobenzidine (Sigma) in $H_2O_2$. Screening of Western blots with 2-D separated human proteins with fertile and infertile sera was performed by blocking and washing as described above prior to incubation with pools of 5 individual's sera.

Protein Microsequencing

Sequencing was performed by the W.M. Keck Foundation Center for Biomedical Mass Spectrometry. Briefly, protein spots were cut from the polyacrylamide gel as closely as possible, minced, washed and dried in 50% methanol before dehydration in acetonitrile and rehydration in 50 μl of 10 mM dithiothreitol in 0.1 M ammonium bicarbonate for 1 hr at 55° C. The sample was alkylated in 50 μl 50 mM iodoacetamide and 0.1M ammonium bicarbonate in the dark for 1 hr at room temperature before 2 rounds of washing with 0.1 M ammonium bicarbonate and dehydration in acetonitrile prior to vacuum dessication and treatment with 12.5 ng/μl trypsin in 50 mM ammonium bicarbonate on ice for min. After removal of any excess trypsin solution 20 μl of ammonium bicarbonate was added and the sample was digested overnight at 37° C. before extraction of the peptides in 50% acetonitrile/5% formic acid and analysis LC-MS analysis. Edman degradation was performed on a PE Biosystems Model 494 according to manufacturer's instructions.

RT-PCR

Oligonucleotides designed from the EST and cDNA library clones were manufactured by GibcoBRL. Oligonucleotides (EST forward primer: 5'-CTTGCT-CTAGCAGCAGCAGAAC-3' (SEQ ID NO: 3); EST reverse primer: 5'-TCATAACACATGACACATAAAG-ATGTTGGC-3'(SEQ ID NO: 4)) to the EST (AA913806) were utilized to generate a 430 bp probe by reverse transcription of human testicular RNA (Clontech). PCR reactions was performed by reverse transcribing 0.05 μg poly-(A)+ RNA in a 20 μl reaction by combining 0.5 μg oligo-d $(T)_{12-18}$ RNA and diethylpyrocarbonate (DEPC)-treated $H_2O$ prior to heating to 65° C. for 5 min. Subsequently, 2 μl 10x RT buffer, 0.5 μl placental ribonuclease inhibitor (36 U/μl; Promega), 1 μl 10 mM 4dNTPs and 1 μl AMV reverse transcriptase (23 U/μl; Stratagene) were added, vortexed and the mixture was incubated for 60 min at 42° C. After the addition of 80 μl DEPC-treated $H_2O$, 1 μl aliquots of the cDNA solution were amplified for 40 cycles with denaturation at 94° C., annealing at 60° C. for 30 sec and polymerization at 68° C. for 3 min, as specified by the recombinant *Thermophilus thermophilus* (rTth) polymerase manufacturer (Perkin Elmer). Separation and isolation of the PCR products was achieved by electrophoresis of reaction aliquots in 1.5% agarose gels made 1x in TAE (40 mM Tris-acetate, 1 mM EDTA) buffer followed by ethidium bromide staining, UV visualization and photography. Collection of specific RT-PCR fragments was performed by electroelution from the agarose gel followed by precipitation, quantitation on agarose gels versus standards and ligation into a pCR2.1-TOPO cloning vector according to manufacturer's instructions (InVitrogen). Sequencing was performed by the University of Virginia Biomolecular Research Facility.

Screening of cDNA Library and Northern Blotting

The sequenced 430 bp insert obtained by RT-PCR was purified by Eco RI-treating the pCR2.1-TOPO cloning vector and collecting the released cDNA fragments by band-excision after agarose gel separation. Fifty ng of the purified fragment was denatured by boiling then radiolabeled with $(\alpha\text{-}^{32}P)$-dCTP by including the two degenerate oligonucleotides described above in the random priming procedure of Feinberg and Vogelstein (1984). The radiolabeled fragment was purified on an Elutip-D column (Schleicher and Schuell) and hybridized to six 137 mm plaque lifts (Magna Nylon Transfer Membranes, MSI) containing a total of 240,000 phage from a human testicular λDR2 5'-stretch cDNA library (Clontech) in a solution containing 50% Formamide, 5xSSC, 5x Denhardt s Solution, 0.25 μg/ml yeast RNA, 0.5% SDS and 0.05 M sodium phosphate (pH 7.0) at 42° C. After overnight hybridization the filters were washed in a final solution of 0.2xSSC/0.2% SDS at 52° C. before mounting, exposure to XAR-5 film (Kodak) and development. Twenty primary isolates were rescreened twice and the remaining 8 positives were converted from λDR2 to pDR2 according to manufacturer's instructions in AM1 cells. Sequencing was performed by the University of Virginia Biomolecular Research Facility in both directions and the nucleotide and amino acid data were analyzed using the Genetics Computer Group and SEQWeb (Madison, Wis.) program packages.

To generate a probe for tissue specificity analysis 50 ng of the purified full-length 1337 bp C7/8 cDNA was radiolabeled as described above except for the omission of the EST oligonucleotides. The radiolabeled cDNA was isolated and hybridized in ExpressHyb (Clontech) to either a Human Multiple Tissue Northern (Clontech) or a Human RNA Master Blot (Clontech). All prehybridizations, hybridizations and washings were performed according to manufacturer s instructions. The Human Multiple Tissue Northern contained 2 μg of poly-(A)+ RNA from spleen, thymus, prostate, testis, ovary, small intestine, mucosal lining of the colon and peripheral blood leukocytes per lane while the Human RNA Master Blot contained various amounts (100–500 ng) of poly-(A)+ RNAs from 76 different tissues normalized to various housekeeping genes.

Expression and Isolation of Recombinant Human C7/8

The C7/8 ORF minus the leader peptide was adapted for ligation into pET-28b+ by designing adaptor-primers containing in-frame Nco I and Xho I sites in the 5'- and 3'-primers, respectively. The complete 1337 bp cDNA containing both the 5'- and 3'-UTRs was subjected to PCR (see above) with rTth DNA polymerase according to manufacturer's instructions (Perkin-Elmer) along with C7/8/pET-28b+/Forward (5'-CATGCATGCCATGGATCCGAGC-ATAACTGTGACACCTGATGAA-3') (SEQ ID NO: 5) and C7/8/pET-28b+/Reverse (5'-GAGTCGCTCGAGAT-AAACTTTTAATAAGGCTGTGACTCTCCTTG-3') (SEQ ID NO: 6) primers. After pET-adaption PCR was performed on the C7/8 cDNA fragment and the resulting products separated on a 1.0% agarose gel, a 990 bp band was collected, restricted along with the pET-28b+ vector with Nco I and Xho I, reisolated on an agarose gel, ligated into the restricted pET-28b+ vector and transformed into Novablue (DE3) host cells. Recombinants were screened by direct ethidium bromide visualization (Data not shown) of restricted plasmid preparations and a clone was chosen for sequencing by the University of Virginia Biomolecular Research Facility using primers surrounding the pET-28b+ vector cloning site to ascertain the proper insertion of the insert into the pET-28b+ expression vector and the retention of the leaderless-C7/8 reading frame.

Recombinant human C7/8 (rec-h-C7/8) containing a C-terminal $(HiS)_6$-Tag was isolated by resuspending the bacterial cell pellet in a Binding Buffer (5 mM imidazole, 0.5 M NaCl, 20 mM Tris (pH 7.9)) prior to sonication and centrifugation. The pellet containing the insoluble protein fraction and inclusion bodies was then resuspended in Binding Buffer made 6 M in urea, incubated on ice for 1 hr, resonicated and recentrifuged prior to filtering the resulting supernatant through a 0.45 m filter. The filtered bacterial protein lysate was then bound to a 5 ml bed-volume His-Bind Resin (Novagen) column prepared according to manufacturer's instructions and washed until the $OD_{280}$ approached baseline with Binding Buffer containing 6 M urea before washing the column to baseline with Wash Buffer (40 mM imidazole, 0.5 M NaCl, 20 mM Tris (pH 7.9) and 6 M urea). Final purification of the rec-h-C7/8 was accomplished by elution from the column with Elute Buffer (300 mM imidazole, 0.5 M NaCl, 20 mM Tris (pH 7.9)) and dialysis into 1×PBS prior to loading onto a Prep-Cell.

Large-scale preparation of purified recombinant human C7/8 (rec-h-C7/8) was performed and the protein was prepared and solubilized. The rec-h-C7/8 was bound and batch-eluted from His Bind (Novagen) resin according to manufacturer's instructions. After column purification of the recombinant material the resulting eluted column fraction is greater than 99% pure. The partially purified rec-h-C7/8 was subjected to Prep-Cell electrophoresis resulting in the final product. The yield of the purified recombinant h-tekB1 was judged by SDS/PAGE electrophoresis to be approximately 1.7 mg of rec-h-tekB1/liter fermentation.

Generation of Rat Monospecific Polyclonal Sera

Nine young adult, female, virgin Lewis rats were immunized in three groups with 100 μg of purified rec-h-C7/8 in either Complete Freund s Adjuvant, alum or squalene monooleate. After 1 month each group of 3 rats was boosted twice at 2 wk intervals with 50 μg of rec-h-C7/8 in with the corresponding adjuvant and bled 1 wk after each boost. Specificity of the rat antisera for rec-h-C7/8 (α-rec-h-C7/8) was tested by Western blotting against rec-h-C7/8 as well as a SDS lysate of human sperm proteins separated on polyacrylamide gels and Western blotted.

EXAMPLE 2

Isolation of SAMP32

TritonX-114 Phase Partitioning and Two-dimensional Gel Electrophresis and Vectorial Labeling by Biotin Human semen samples were obtained from healthy donor (s) as described (Mandal et. al., 1999). Triton X-114 phase partitioning was done according to Bordier (Bordier, 1981). Two-dimensional gel electrophresis was conducted as described in Example 1. Proteins were biotin labeled using standard techniques.

SDS-PAGE and Western Blot

Proteins were separated first on discontinuous polyacrylamide gel (4% stacking and 15% separating gel) at 100 volts voltage constant on a Bio-Rad mini-gel apparatus (Bio-Rad, California). Gels were then either stained with Coommassie blue or used for transfer to the membrane in western blot. For the western blot, proteins were transferred to Nitrocellulose membrane (0.2 um) at 100 volts voltage constant for one hour with cooling. At completion, membranes were blocked in PBST containing 5% non-fat milk, and 1% normal goat serum for one hour at room temperature on a rocking platform. This procedure was followed by incubation of the membrane in PBST containing 5% non-fat milk, 1% normal goat serum and 1:2,000 to 1:4,000 of primary antibody for another hour. After three washes of the membrane(s) with PBST, each for 10 min, the membranes were incubated further with PBST containing 5% non-fat milk 1% normal goat serum and 1:4,000 diluted secondary goat antibody conjugated to HRP. Following three washes of the membrane(s) with PBST, the color was developed by adding TMB substrate at room temperature.

Screening of Lambda cDNA Library.

Lambda DR2 cDNA library from human testis was purchased from Clontech Inc. (Palo Alto, Calif.) and screened according to the user manual. Briefly, a total of $2.5 \times 10^5$ clones were plated out on six 150 mm agar plates on a bacteria lawn. After replica plate onto the nylon membrane, phage particles were denatured in 0.5 M NaOH, 1.5M NaCl; and neutralized in 0.5M Tris pH 7.5, 1.5M NaCl. Following UV cross-link, the filters were washed in 2×SSC, 0.2% SDS for 20 min at room temperature, prehybridized for 4 hours at 42° C. in hybridization solution, without the probe, and hybridized at 42° C. overnight in the presence of 50% formamide. The 3' 420 bp cDNA fragment, amplified and cloned from the human testis EDNA library, was used as a probe after labeling with $^{32}$P-dCTP by random primer method. Washes were done once in 2×SSC, 0.2% SDS for 20 min at RT, once in 0.2×SSC, 0.2% SDS for 20 min at 42° C., and once in 0.2×SSC, 0.2% SDS for another 20 min at 50° C. At the end of the washes, the filters were exposed on X-ray film at −80° C. for 24 to 48 hours before development. Secondary screening was repeated as above to isolate single, pure phage plaques. Finally, the cDNA inserts were recovered as plasmids in pDR2 vector from the phage particles by transforming the *E. coli* AM1 strain expressing Cre recombinase. This process was made possible by the presence of two phage P1 derived lox-P recombination sites at both ends of the cDNA insert.

Polymerase Chain Reaction (PCR) and Rapid Amplification of cDNA Ends(RACE)

Polymerase chain reactions were done following standard conditions (Hao et. al., 1997). Hot start PCRs using the library template and for RACE were performed by using the Amp-Taq DNA polymerase from Perkin-Elmer. The parameters used were 94° C. 10 min, 94° C. 30 sec, 55° C. 30 sec, and 72° C., 2–4 min for 35–40 cycles. PCRs using plasmid template were done using cloned pfu DNA polymerse from Stratagene (parameters were the same except the denaturation was 5 min before cycling and the cycle number was 30 cycles). The primers used to amplify the probe for plaque and northern blot hybridization were Hao1 (AGTCACCCCTTGGCTTTCGAGT; SEQ ID NO: 10) and Hao2 (AATATTCTGTAATATCCTTTGGTT; SEQ ID NO: 11). The primers for SAMP32 3' amplification of were Hao39 (CTTTGTATGTCACATTCCCTGAAG; SEQ ID NO: 12) and Hao41 (GAGGTACAATCCGAGCAGAGT-TCT; SEQ ID NO: 13) or Hao41 and AP1 primer supplied in the Marathon ready cDNA kit (Clontech).

Northern and Dot Blot

Human multiple tissue northern membrane containing 8 tissues and Multi-tissue array RNA dots containing 67 tissues were purchased from Clontech Inc. The same 3' 420 bp cDNA described above was used as probe. Hybridization was performed in ExpressHyb™ solution at 68° C. for 1 hour and washed successively two times in 2×SSC, 0.1% SDS each for 20 min at room temperature; and three times in 0.1×SSC, 0.1% SDS each for 20 min at 65° C. Films were exposed 24 to 72 hours at −80° C. The same membrane was probed with beta-actin supplied in the kit after stripping out the previous probe.

To probe the multi-tissue array RNA dots, the same 420 bp of DNA was labeled and hybridization was done at 68° C. overnight in ExpressHyb solution containing salmon sperm ssDNA and Cot-1 DNA overnight, following manufacturer's instruction. The film was exposed 96 hours at −80° C.

Expressing Recombinant Protein in E. coli and Production of Antiserum

To express SAMP32 in E. coli, the fragment that contains amino acid 30–221 of the open reading frame was amplified by PCR. It was then fused in frame with the H is-tag at both ends of pET28b using the NheI and XhoI sites. Construct was verified by DNA sequencing. Due to the codon bias, Epicurian Coli BL21-CodonPlus™ cells were used as the host strain (Stratagene) in the place of conventional BL21 DE3. The plasmid was transformed into the host strain and a large culture derived from a single colony, was grown to OD600=1.0 at 37° C. in LB in the presence of 50 ug/ml of Kanamycin. Isopropyl-1-thio-beta-D-Glactopyranoside (ITPG) was then added to a final concentration of 1 mM to induce expression. After a further 3 to 4 hours of growth, the bacteria were collected by centrifugation for recombinant protein processing. The recombinant protein was affinity purified with Ni-NTA column in denatured condition. Preparative gel electrophresis couple with Elutip™ was employed to remove minor contaminant proteins from E. Coli.

Female virgin Lewis rats, weighing 160–200 grams, were used in antiserum production. Purified recombinant protein in PBS was emulsified with equal amount(s) of Freud's complete adjuvant and each rat was injected with 100 ug of protein in 0.3 ml s.c. initially. The same amounts of protein, emulsified with equal volume of Freud's incomplete adjuvant, were given by the same route in subsequent booster injections at two weeks interval. The antibody titers were checked by western blot analysis 10 days after each booster injection. The animals were sacrificed soon after a check indicated a titer above 1:2000 on total sperm extract western.

Immunofluorescence of Enzyme Dissociated Tissue

Human testis block was cut and dissociated with collagenase, micrococcal nuclease and trypsin. Dissociated cells were spread out on slides and dried. The slides were washed in PBS trice, permeablized in Methanol, and washed again with PBS. The slides were blocked in 10% normal donkey serum for 1 hour. They were then incubated with antibody solution containing 1% normal donkey serum and 1:100 to 1:200 dilution of rat anti-SAMP32 antiserum overnight at 4° C. After three washes with PBST containing 1% normal donkey serum, the slides were incubated with secondary antibody (donkey anti-rat conjugated with TRITC, 1:200 in PBST and 1% normal donkey serum) for 60 min. The slides were washed twice with PBST, twice with PBS, and fixed with 2% paraformaldehyde for 10 min. After washing with PBS, they were incubated in equilibration buffer. Nucleus were stained with DAPI and slides were mounted with Slow-Fade anti-fade reagent (Molecular Probes). Images were captured using a Zeiss Axioplan2 microscope equipped with epifluorescence using Open Lab software (Improvision).

Preparation of Spermatozoa and Acrosomal Reaction

Human semen samples were obtained from healthy donors and Swim-up sperm was prepared as follows. Freshly ejaculated semen samples were liquidified for 30 min to 1 hour at room temperature. They were diluted with an equal volume of BWW and centrifuged at 500 g for 5 min to remove seminal plasma. The sperm pellets were washed twice with BWW containing 10 mg/ml of BSA (500 g×5 min). Following the removal of supernatant, the sperm pellets were overlaid carefully with BWW containing 30 mg/ml of human serum albumin. The sperm samples were then incubated at 37° C. for 1 hour to allow the sperm to swim up. Sperm were then incubated in BWW in the presence of calcimycin to induce aersomal reaction at 37° C.

Immunofluorescence Localization of SAMP32 in Sperm and Electron Microscopic Analysis The sperm were air-dried onto Poly-L-Lysine coated slides (Polysciences, Warrington, Pa.). They were permeabilized in methanol, air-dried and blocked in 10% normal goat serum in PBST for 30 min. The sperm were then incubated with 1:100 dilution of anti-SAMP32 primary antiserum for 2 hours at 37° C. Following incubation with the secondary goat-anti-Rat IgG conjugated with Cy3 at 1:100 dilution for 1 hour at 37° C., the slides were washed in PBS, coated with slow-fade, and mounted in coverslips.

For immuno-electron microscopy, pooled sperm were washed twice in Ham's F-10. containing 3% sucrose. They were then fixed in 4% paraformaldehyde and 0.2% glutaraldehyde in wash buffer for 15 min at 22° C. The fixatives were removed by washing and the sperm were dehydrated by passing through a series of graded ethanol, ranging from 40% to 100%. Following embedding in Lowicryl K4M, the blocks were polymerized with UV light at −20° C. for 72 hours and ultra-thin sections were cut. To stain the ultra-thin sections, they were first blocked in undiluted normal goat serum for 15 min at 22° C. They were then incubated for 16 hours at 4° C. with either preimmune or rat-anti-SAMP32 antiserum at the dilution of 1:50 containing 1% normal goat serum, 1% BSA and 0.1% Tween-20. After washing, the sections were then incubated with 1:100 dilution of 5 nm gold-conjugated goat-anti IgG (Goldmark Biologicals, Phillipsburg, N.J.) for 1.5 hours at 22° C. The sections were washed in distilled water and stained with uranyl acetate and observed with the JOEL 100CX electron microscope.

EXAMPLE 3

Isolation of C58

Separation of Hydrophobic, Putative Sperm Membrane Associated Proteins by TX-114—Phase Partitioning To isolate the hydrophobic, putative membrane associated sperm proteins, TX-114—phase partitioning was conducted. In particular, human sperm cells were solubilized in 1.7% TX-114/TBS at 4° C. The solution was cetrifuged and the supernatant containing the solubilized proteins was recovered. TBS was added to adjust the TX-114 concentration to 1.%. Warming to 30° C. allowed the aggregation of micelles and separation of detergent phase from the aqueous phase. The two phases were separated by centrifugation.

2-D electrophoresis was used to analyze the phase partitioned sperm proteins. The starting total extract, aqueous phase extract, and detergent phase extract were analyzed by 2-D gel electrophoresis. TX-114 phase partitioning allowed the selective partitioning of several hydrophobic proteins to the detergent phase. C58 is one of the 2-D protein spots enriched in the hydrophobic detergent phase extract.

To determine if C58 is a surface protein, freshly harvested human sperm cells were vectorially labeled with sulfo-NHS-LC biotin, subjected to TX-114 phase partitioning and the detergent phase extract obtained was separated by 2-D gel electrophoresis. Protein spots labeled with biotin were visualized by avidin-ECL and compared to a silver stained companion gel to identify the biotinylated protein spots. The 2D gels indicated that C58 is vectorially labeled with sulfo-NHS-LC biotin, and thus C58 is probably located on the surface of the sperm.

The C58 spot excised from a Coomassie stained 2-D gel was microsequenced using tandem mass spectrometry. Four peptide sequences were isolated. Data base search analysis done using the tryptic peptides revealed no matches to any known proteins. However, two of the peptides matched to a Human testis EST clone (AC. No. AA778671; SEQ ID NO: 17).

Cloning of C58 cDNA Utilizing EST cDNA Sequence

Human testis EST (AC NO. AA778671) matching to tryptic peptides obtained from microsequeincing of spot C58 was amplified by PCR. The PCR cDNA fragment was verified and then labeled with $^{32}$P and used to screen a λ-DR2-testis cDNA library. Positive clones were isolated and sequenced. The cDNA for the complete open reading frame of C58 was obtained (SEQ ID NO: 14). The Complete ORF of C58 contained 372 base pairs encoding 124 amino acids with a predicted Mol Wt. of 13 and a predicted pI of 5.5. Sequences of one of the tryptic peptides originating from the cored 2-D spot was found embedded in the ORF (ATSCGLEEPVSYR; SEQ ID NO: 19). Alignment of amino acid sequence of C58 with other proteins having a similar domain utilizing a bioinformatic program 'Multi-align' revealed several conserved cysteine residues were found among the group of proteins showing similarity to C58, The conserved position of the cysteine residues, which may be involved in the formation of disulfide bridges, suggests a potential conserved function secondary and tertiary structure to these proteins. Internal sequence of all proteins showed similarity to the Ly-6/UPAR superfamily of proteins.

C58 Shows homology to Ly6D (E48 Antigen)_Human (see FIG. 3). Ly6D is expressed exclusively at the outer cell surface of transitional epithelial and the keratinocytes of stratified squamous epithelial carcinoma. The protein is attached to the cellular membrane by a GPI-anchor. The Ly6D protein contains a 1UPAR/Ly-6 Domain and is believed to be involved in cell-cell adhesion and signal transduction.

A bioinformatic analysis of amino acid sequence of C58 was done to check the possibility of it being a Glycosyl Phosphatidyl Inositol anchored protein. The structure of C58 indicates that the protein is a GPI anchored Protein. In particular, C58 has a transmembrane N-terminal signal peptide (amino acids 1–19 of SEQ ID NO: 16), a transmembrane C-terminal hydrophobic domain and a transamidase cleavage site (located at amino acids 97–99 of SEQ ID NO: 16) near the C-terminal end typical of a GPI anchored protein. Amino acids 22–112 of C58 (SEQ ID NO: 16) include a Ly-6 Antigen/Urokinase Plasminogen Activator receptor-like domain.

Northern Blot Analysis for Tissue Specificity

A standard Northern blot analysis was done by using Clontech's multiple tissue northern blot analysis panel of 8 human tissues (see FIG. 4). cDNA from the entire open reading frame of C58 was used as the probe (radiolabeled with $p^{32}$) and hybridized to 2 ug poly-(A)+ mRNAs isolated from spleen, thymus, prostate, testis, ovary, small intestinem colon and leucocyte and located in lanes 1–8, respectively. Size of molecular weight markers is indicated at left. A positive signal was obtained in the testis lane only for standard Northern blot analysis. A MTE array Northern blot analysis of 76 tissues was done also using cDNA from entire ORF of C58 as the probe. Similarly a 76 dot-blot Northern blot analysis also yielded a prominent signal in the testis box only. Thus the message for C58 is transcribed in testis only.

Recombinant Expression of C58

Two different constructs were made for the recombinant expression of C58 using vector pET 28b. Construct 1 (C58-1): cDNA corresponding to aa 20–124 was engineered into the vector with a histidine tag at the C-terminal end. Construct 2 (C58-2): cDNA corresponding to aa 20–100 was engineered into the vector with a histidine tag at the C-terminal end. The constructs were trasfected into E. coli and a small scale culture of the host cells BL21-pLys S-DE3 containing vector pET 28b with or without insert (Control) were induced with 1 mM IPTG and harvested after 4 hours. Bacterial lysates made in Laemmli buffer were run on 16% SDS-PAGE. The electrophoresed proteins were Coomassie stained or transferred to a nitrocellulose membrane and probed with Ni-NTA (1:2K) to visualize expressed protein.

Upon induction, additional bands of proteins were visualized on a Coomassie stained gel on the induced lanes corresponding to C58-1 and C58-2, which also reacted with Ni-NTA on a western blot. The bands appeared at the expected molecular weight range of 9.5–14 kDa.

Four-liter cultures of host cells expressing C58-1 and C58-2 were made and induced with 1 mM IPTG. The expressed proteins were partially purified by His-column chromatography. The proteins were further purified by electrophoretic purification using Prep Cell (BioRad). Samples from all the fractions were analyzed by SDS-PAGE. His-Column chromatography followed by Prep Cell purification allowed the purifaction of expressed protein.

Western Blotting Analysis of Recombinant C58 and Human Sperm Proteins with Anti-Rat Antibody for Recombinant C58.

Human sperm proteins were solubilized in Celis extraction buffer. The supernatant was mixed with equal volume of 2× Laemmli buffer. Samples of recombinant proteins were prepared by directly solubilizing the lyophilyzed powder of recombinant C58 (+transmembrane domain; (TM)) and C58 (–TM) in 1× Laemmli buffer. Samples were run on 16% SDS-PAGE. The proteins transferred to a nitrocellulose membrane were probed with preimmune (PI) and immune (IM) serum from rat #2 for C58 (+TM) and rat #17 for C58 (–TM). Blots were incubated with secondary antibody (goat anti rat IgG) and developed by using TMB membrane peroxidase substrate. Strips were also incubated directly with secondary antibody (sec. Ab con) to visualize any non-specific proteins reacting with secondary antibody alone.

Antibodies for both C58 (+TM) and C58 (–TM) recognized the respective recombinant proteins. Both antibodies recognized a single band at approximately 12.5 kDa on the sperm protein blots indicating that the antibodies are recognizing the native C58 protein.

Western Blot Analysis of Human Sperm Proteins Separated by 2-D Gel Electrophoresis Using Anti-Rat Recombinant C58 Antibody.

Human sperm proteins were solubilized with Celis extraction buffer, separated by 2-D gel electrophoresis and transferred to nitrocellulose membrane. The proteins were stained with protogold to visualize total separated proteins. The blots were probed with anti-rat antibody for recombinant C58 (−TM) (rat #17) at 1:4K. The blots were incubated with secondary antibody and the reactive spots were visualized using TMB membrane peroxidase substrate.

The antibody reacted with the native C58 spot that was initially cored for microsequencing. In addition to recognizing the cored protein it also recognized 2 small additional spots on either side at the same molecular weight range suggesting the possibility of the protein having charge variants Indirect Immunofluorescence Localization of C58 on Air-dried Human Sperm Using Anti-Rat Recombinant C58 (+TM) Antibody.

Human sperm were prepared by swim-up method, and air-dried on slides at a concentration of $\sim 2 \times 10^6$. The sperm were blocked with 10% normal goat serum in PBS and incubated with anti-rat antibody (rat #2) for C58 (+TM) at 1:30 dilution. The slides were washed in PBS and incubated with FITC conjugated goat anti-rat IgG. Then they were washed in PBS and mounted using antifade.

Sperm incubated with immune serum showed signal over the entire surface of the sperm with higher reactivity localized to the head. There was no fluorescent signal observed with the sperm smear incubated with preimmune serum. The results indicated that C58 is located on the surface of the sperm

EXAMPLE 4

Human Sperm Binding and Fusion Assay Using Zona-Free Hamster Eggs

Sperm Preparation:

Motile sperm were harvested by the swim up method of Bronson and Fusi (1990). Briefly, a 500 ml sperm sample underlaid in 2 ml of BWW media containing 5 mg/ml HSA. Sperm were allowed to swim up for 1.5–2 h. Swimup sperm were collected and 8 ml of BWW+5 mg/ml HSA was added. The composition was spin at 600×g for 8 min at RT, the supernatant was removed and 8 ml of media was added to the pellet. The resuspended pellet was spun at 600×g for 8 min at RT. The supernatant was removed and 50 ml of BWW containing 30 mg/ml HSA was added to the pellet. Total sperm cells were counted and then incubated overnight in BWW+30 mg/ml HSA at a concentration of $20 \times 10^6$ sperm/ml.

Egg Collection:

Female hamsters received i.p. injections of 30 IU PMSG followed by 30 IU of hCG 72 h later. 14–16 h following hCG injection, hamsters were sacrificed. and oviducts are collected in BWW media containing 5 mg/ml HSA. Cumulus cells were removed with 1 mg/ml hyaluronidase, the eggs were washed and zona pellucidae removed with 1 mg/ml trypsin. The eggs were then thoroughly washed and allowed to rest in the incubator.

Sperm/Antibody Incubation:

Sperm was diluted to $20 \times 10^6$ sperm/ml and incubated with appropriate dilutions of pre-immune or immune sera (initially a 1:10 and 1:50 dilution of sera is tested) in paraffin oil covered microdrops for 1 h.

Hamster eggs were added to the drops containing the sperm+antibody. The gametes were then co-incubated for 3 h.

Assessment of Binding and Fusion:

Eggs were washed free of unbound and loosely bound sperm by serial passage through 5 (50 ml) wash drops. The same pipet is used for all eggs washed in an individual experiment. Eggs are then stained by short-term (5–15 s) exposure to 1 mM acridine orange-3% DMSO in BSA/BWW (30 mg/ml), washed through 4 (50 ml) wash drops and mounted under 22×22 mm coverslips. Under UV illumination, unexpanded head s of oolemma-adherant sperm were counted and sperm that had penetrated the ooplasm exhibited expanded green heads. All experiments were repeated 3 times

| 1:10 dilution of C 71 Antibody | | | |
|---|---|---|---|
| Number of sperm bound per egg | | | |
| Pre Immune | 24.2 | Immune | 11.5 |
| | P value = 6.6 × 10⁵ | | |
| Number of sperm fused per egg | | | |
| Pre Immune | 2.2 | Immune | 0.35 |
| | P value = 1.8 × 10⁶ | | |
| 1:10 dilution of C7/8 Antibody | | | |
| Number of sperm bound per egg | | | |
| Pre Immune | 13.7 | Immune | 7.9 |
| | P value = 0.003 | | |
| Number of sperm fused per egg | | | |
| Pre Immune | 1.8 | Immune | 0.59 |
| | P value = 9.63 × 10⁵ | | |

What is claimed is:

1. A purified or recombinant polypeptide comprising an amino acid sequence of SEQ ID NO: 2.

2. A nucleic acid sequence comprising the sequence of SEQ ID NO: 1.

3. A transgenic host cell comprising a recombinant gene, said gene comprising the nucleotide sequence of claim 2.

4. The polypeptide of claim 1, wherein said polypeptide is bound to a solid support.

* * * * *